(12) United States Patent
Gage et al.

(10) Patent No.: US 6,326,484 B1
(45) Date of Patent: Dec. 4, 2001

(54) NUCLEIC ACIDS ENCODING REGULATORS OF FGF-2 TRANSCRIPTION (RFT) AND VARIANTS THEREOF

(75) Inventors: Fred H. Gage, La Jolla, CA (US); Tetsuya Ueba, Kyoto (JP)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/079,431

(22) Filed: May 14, 1998

(51) Int. Cl.⁷ .............................. C07H 21/04; C07H 21/02
(52) U.S. Cl. .......................................... 536/24.1; 536/23.1
(58) Field of Search .................................... 536/23.1, 24.1

(56) References Cited

PUBLICATIONS

Cross et al. Nature Genetics, vol. 16, pp. 256–259, Jul. 1997.*
Kennell Progr. Nucl. Acid Res. Mol. Biol., vol. 11, pp. 259–301, 1971.*
Yoshikawa et al. Am. J. Med. Genetics, vol. 74, pp. 140–149, Apr. 1997.*
Cross et al., H.sapiens mRNA for protein containing MBD1, Accession #Y10746, US National Library of Med., Accessed by PTO Oct. 22, 1999, Jul. 1997.*
Yoshikawa et al. human brain ARSanders cDNA clone 26903 mRNA, Accession #U55972, US National Library of Med., Accessed by PTO Oct. 25, 1999, Apr. 1997.*
Hillier et al., "The WashU–Merck EST Project," Accession No. H85883.

* cited by examiner

*Primary Examiner*—Deborah J. R. Clark
*Assistant Examiner*—Michael C. Wilson
(74) *Attorney, Agent, or Firm*—Knobbe, Martens, Olson & Bear, LLP

(57) ABSTRACT

The present invention is based on the discovery of genes which encode polypeptides are FGF-2 regulators of transcription (RFT). RFT-A, a negative regulator of transcription and RFT-A' and RFT-B, positive regulators of FGF-2 traniscriptionl are provided. Also included are methods for diagnosis of prognosis for a subject having or at risk of having a disorder associated with FGF-2 and for treatment of cell proliferative disorders associated with FGF-2. Screening methods for identifying a compound which affects RTT-A polypeptide or a variant of RFT-A polypeptide and for identifying proteins that bind to RFT-A polypeptide or a variant of RFT-A are also provided.

15 Claims, 12 Drawing Sheets

FIG. 1A-1

```
DNASIS Translation Editor (FTF-A)
   1 GAACAGCCGCGGAGGCGACAGCTACCGCTTCAGAGAGGAGCCCGGAGGAGGAGAAG          60
  61 GGGAGGAGGCGAGGGCGAGGTGCAGGAGGACCCTCGCCATGGTCCACGGCCTAGA         120
 121 GTGGCGGAAGATACCGGCCTGGTGCCAAACTGGCTACTGCTGCTTCCTGTGGCCTCCATG    180
                                                              M
 181 GCTGAGGACTGGCTGCCCGGCCCCTGGCTGGAAGCGCCGCGAAGTCTTT               240
       A  E  D  W  L  P  G  P  A  L  G  P  G  W  K  R  E  V  F       21
 241 CGCAAGTCAGGGGCCACCTGTGACGCTCAGACTATACCAGACCCCACAGGAGAC          300
       R  K  S  G  A  T  C  D  A  Q  T  Y  Y  Q  S  P  T  G  D       41
 301 AGGATCCGAAGCAAAGTTGAGCTGACTCGATACCTGGGCCCTGCGTGTGATCTCACCCTC    360
       R  I  R  S  K  V  E  L  T  R  Y  L  G  P  A  C  D  L  T  L    61
 361 TTTGACTTCAAACAAGGCATCTTGTGCTATCCCAGCCCCAAGGCCCATCCCGTGGCGGTT    420
       F  D  F  K  Q  G  I  L  C  Y  P  S  P  K  A  H  P  V  A  V    81
 421 GCCAGCAAGAAGAAGAAAGCCTTCAAGGCCTTGAAACTCGAAACGTCAGGTTGGA        480
       A  S  K  K  K  K  A  F  K  R  P  A  K  T  R  K  Q  V  G       101
 481 CCCCAGAGTGGTGAGGTCAGGAAGGAGCCCCGAGGGATGAGAGAACTGTGAGAATCAGCTGAC  540
       P  Q  S  G  E  V  R  K  E  A  P  R  D  E  N  C  S  F  S       121
 541 ACAGCCCCAGCTTCATTCCCTGCCAGCAGCCCAAAAGCTTGTGCAAAGTTGTGAGCACAGAGA  600
       T  A  P  A  S  F  I  P  A  S  S  P  K  L  C  K  D  C  R  R    141
 601 GGGGATGGCACCCACCCAAACGGAACAGAATGTTTAAGCGTGTGGGCTGTGTGCCTGCAGCC  660
       G  D  G  T  H  P  N  R  N  R  M  F  K  R  V  G  C  V  Q  A    161
 661 ATTGCCCTTCAAACAGAAACTGTCTGCTCCAACCTCCCTGCCTGCCCTCCTGCTTTATGAT  720
       I  A  F  Q  T  E  T  V  C  S  T  C  L  L  Q  L  P  H  D       181
 721 TGCCAGGTAACAGATCGGGCTGTTCTGCAAGTGTGAACGGAGACGCTGCCTCCGAGGATTGTGGAAAGG  780
       C  Q  V  T  D  R  A  V  L  Q  V  *  T  G  D  A  A  S  E  D  V  E  R  201
 781 GTGGCATCGGGCTGTGAGTATGCCAAGGATTGTGGCCATTGCCCC                   840
       V  A  S  G  L  *  V  C  Q  R  C  Q  T  Q  E  D  C  G  H  C  P    221
 841 AGCCGAGGGTGTGAGTATGCCAAGGATTGTGGCCATTGCCCC                      900
       S  R  G  V  *                                                     241
```

DNASIS Translation Editor (FTF-A)

```
1741 CAGGTGAAGCAAGAGAAGGCGGATACCCAGGACGAGTGGACACCAGGCACAGCTGTCCTG 1800
 521   Q  V  K  Q  E  K  A  D  T  Q  D  E  W  T  P  G  T  A  V  L   541
1801 ACTTCTCCCGTATTGGTGCCTGCCTGCCCAAGGCAGTAGACCCAGGCCTGCCTTCT 1860
 541   T  S  P  V  L  V  P  G  C  P  S  K  A  V  D  P  G  L  P  S   561
1861 GTGAAGCAAGAGAGCCACCTGACCCAGAGGAGAAGGAGAACAAGGATGATTCTGCC 1920
 561   V  K  Q  E  S  H  L  T  Q  E  E  D  K  E  E  N  K  D  S  A   581
1921 TCCAAATTGGCCCCCAGGAAGAGAGGCAGGAGGGGCTGGCACACCCGTGATCACGGAGATT 1980
 581   S  K  L  A  P  R  K  E  E  A  G  G  A  G  T  P  V  I  T  E  I   601
1981 TTCAGCCTGGGTGGAACCCGCTTCCGAGATACAGCAGTCTGGTTGCCAAGGTCCAAAGAC 2040
 601   F  S  L  G  G  T  R  F  R  D  T  A  V  L  P  R  S  K  D   621
2041 CTTAAAAAACCTGGAGCTAGAAAGCAGTAGACTGGAGGCTTCTACAGACTGTAGGATTCA 2100
 621   L  K  K  P  G  A  R  K  Q                                     630
2101 AGGTGATATTTGCAGACTGGCTTTATGAGAGACAACACTGATCTACTAGGGGCTGGACCC 2160
                                                                      630
2161 TACATTGGTTGCCAGGGCTTGTGTGTGAATCACCCCCTAGAGGAAAAACCTACTATCAAA 2200
                                                                      630
2221 CCTGAAGAGCAGGCCCTAAGAGTACTTTGAGCTTCTAG                         2257
                                                                      630
```

FIG. 2A-1

```
DNASIS Translation Editor (FTF-A')
   1 GAACAGCCGCGGAGGCGACAGCTACCGCTTCAGAGGAGGCGCCGGAGGAGGAGGAAG          60
                                                                         1
  61 GGGAGGAGGGCGAGGCGAGGTGCAGGAGGACCCCTCGGCCATGGTCCACGGCCTAGA         120
                                                                         1
 121 GTGGCGGAAGATACCCGGTCGTGCCAAACTGGCTACTGCTGCTTCCTGTGGCCTCCATG        180
                                                                  M      1
 181 GCTGAGGACTGGCTGGACTGCCCGGCCCTGGCTGGAAGCGCCGCGAAGTCTTT             240
       A  E  D  W  L  D  C  P  A  L  G  P  G  W  K  R  E  V  F         21
 241 CGCAAGTCAGGGGCACCCCTGTGGACGCTCAGAGACGCTATTACCAGACCCCACAGGAGAC     300
       R  K  S  G  A  T  P  C  D  A  Q  R  R  Y  Y  Q  T  P  R  D      41
 301 AGGATCCGAAGCAAAGTTGAGCTGACTCGATACCTGGGCCCTGCGTGTGATCTCACCCTC      360
       R  I  R  S  K  V  E  L  T  R  Y  L  G  P  A  C  D  L  T  L      61
 361 TTTGACTTCAAACAAGGCATCTTGTGCTATCTTCCAAGGCCTTCAAGCCGCCATCCGTGGCGGTT  420
       F  D  F  K  Q  G  I  L  C  Y  L  P  A  A  H  P  V  A  V         81
 421 GCCAGCAAGAAGAGCCAAGCGAAAGAAGACTCGGAAACGTCAGGTTGGA                 480
       A  S  K  K  R  Q  A  K  R  K  T  R  K  Q  V  G                 101
 481 CCCCAGAGTGGTGAGGTCAGGAGGAGCCCCTGGGTGCTGTGAGAACTGTCGAGCACACAGAGA   540
       P  Q  S  G  E  V  R  R  S  P  G  C  C  E  N  C  R  A  D  T      121
 541 ACAGCCCCAGCTTCATTCCCTCCCAAAAGGCAGCGGCTCAAAGAGTTTGTGCAAAGAATGTTTAAG 600
       T  A  P  A  S  F  P  A  P  K  A  A  Q  R  L  K  D  C  R  A      141
 601 GGGGATGCCACCCGGGAACCGGCAGAAGAATGTTTAAGCGTGTGGGGCTGTGGGAGTGTGCAGCC  660
       G  D  A  T  R  Q  R  L  K  R  M  F  K  V  W  G  L  W  E  C  Q   161
 661 ATTGCCTTCAACAGAGAACAGACTGTGTGGGGCCCTGCCTCCCTGCCAGCTGCCCCATGAT     720
       I  A  F  N  R  E  Q  T  V  G  A  C  S  T  C  L  P  A  A  M  I   181
 721 TGCCAGGTAACAGAAGACTGTTCTGCAAGTGTGAACGGAGACGCTGCCTCCGGATTGTGAAAGG  780
       C  Q  V  T  E  D  C  S  A  S  V  K  C  E  R  R  C  L  P  D  C   201
 781 GTCCAGTCATCGGGGCTTGTTGGAGTGGAGTATGCCCAAGACCCAGACCCTGTGCAAGAGG    840
       V  A  S  L  F  G  V  E  Y  A  Q  D  P  V  Q  E  R                221
 841 AGCCGAGGGTGTGCGGGGTGTCAGTGCTGTCAGGGGCCTGTGCAGACCCAGGATTGTGGCCATTGCCCC 900
       S  R  G  V  C  G  V  Q  C  C  Q  G  P  C  R  P  Q  D  C  G  H  C  P  241
```

FIG. 2A-2

```
DNASIS Translation Editor (FTF-A')
 901 ATCTGCCTTCGCCCTCGCCCCGCCCTGGTCTCAGGCGCCAGTGGAAATGTGTCCAGCGACGT  960
 241  I  C  L  R  P  R  P  G  L  R  Q  W  K  C  V  Q  R  R   261
 961 TGCCTACGGCACTTGCTCTGTCGCCGTCATCAGAGATGTCAGCGACGCACT           1020
 261  C  L  R  H  L  A  H  R  L  R  R  E  C  Q  R  R  T         281
1021 CCCCTGGCTGTGTGGCTCCCCCAACTGGTAAAACATGCCAGCAAGGAGGCTGTGACTCC   1080
 281  P  L  A  V  A  P  P  T  G  K  H  A  R  K  G  G  C  D  S   301
1081 AAGATGGCTGCCAGGCGGCGCCCAGAGCGGCCTCCACCACCCCATCACAG           1140
 301  K  M  A  A  R  R  R  P  G  A  Q  P  P  P  P  S  Q         321
1141 TCCCCAGAGCCCACAGAGGACGAGCTACAGCCCTGGCCCCTGCCACCTGCCGAGTTC      1200
 321  S  P  E  P  T  E  P  H  R  A  L  P  A  S  P  A  E  F     341
1201 ATCTATTACTGTGTAGACGAGGACGAGCTACAGCCCTACACGCCGCAGAACCGC         1260
 341  I  Y  Y  C  V  D  E  D  E  L  Q  P  Y  T  N  R  R  Q  R   361
```

FIG. 2B-1

```
DNASIS Translation Editor (FTF-A')
1261 AAGTGCGGGCGGCCTGTGCCAGCCTGCCTACGGCCTGCCGGACTGTGCCGCTGCGACTTCTGC  1320
 361  K  C  G  A  A  C  Q  P  A  Y  G  L  P  D  C  G  R  D  F  C   381
1321 TGCGACAAGCCCAAATTCGGGGCAGCAACCAGAGAAGCGCCAGAAGTGTCGTTGGCGCCAA   1380
 381  C  D  K  P  K  F  G  A  A  T  R  E  A  P  E  V  S  L  A  Q   401
1381 TGCCTGCAGTTTGCCATGCGCCTACCTTGGTCAGAGTGTCTGGAGAGTCTGAGGATGGGCA   1440
 401  C  L  Q  F  A  M  R  L  P  W  S  E  C  L  E  S  E  D  G  A   421
1441 GGATCGCCAGCCCCTACCCTCCTTACCCCGTCGTGGCTCCCCAACCAGCCCACCATCTT    1500
 421  G  S  P  A  P  Y  P  P  Y  P  V  V  A  P  S  S  A  R  H  L   441
1501 GGCCCTACCTTGAAGCAGGAAGCAGGCTACACGCCCTTGGCTACACCAGACCATACCCAGGCT  1560
 441  G  P  T  L  K  Q  E  A  G  Y  T  P  L  A  T  T  Q  A  H  T   461
1561 CCAACGAAGCAGGCAGGCGCAAGCAGTCCTGTGGCTGTGCCGCCTGTGCACTGACCTTGTG  1620
 461  P  T  K  Q  E  A  G  A  S  S  P  V  V  V  P  P  V  H  L  V   481
1621 TTTTACGGGAAGGCAGAGGGCAAGCAGTCCCAGCAGTCCTTAGCAGTTCCACA         1680
 481  F  L  R  E  G  A  S  S  P  V  Q  P  L  A  V  P  Q         501
1681 GAAGCCCTGTTGCAGGAGGCCCTGGCTGTTGGGCCTGGGTTGGTGTGGCCTTACCCCAG      1740
 501  E  A  L  L  Q  E  A  Q  G  L  S  W  V  V  A  L  P  Q         521
```

FIG. 2B-2

```
DNASIS Translation Editor     (FTF-A')
1741 GTGAAGCAAGAGAAGGCGGATACCCAGGACTGGACACCCAGGCACAGCTGTCCTGACT  1800
 521   V  K  Q  E  K  A  D  T  Q  D  W  T  P  G  T  A  V  L  T     541
1801 TCTCCCGTATTGGTGCCTGGCCTAGCAAGGCAGTAGACCCAGGCCTGCCTTCTGTG      1860
 541   S  P  V  L  V  P  G  L  A  S  K  A  V  D  P  G  L  P  S  V  561
1861 AAGCAAGAGAGCCACCTGACCCCAGAGGAGGACAAGGAGAATAAGGATGATTCTGCCTCC  1920
 561   K  Q  E  P  P  D  P  E  E  D  K  E  N  K  D  D  S  A  S     581
1921 AAATTGGCCCCAGAGGAAGAGGCAGGGGGCAGTGGGCACACCCGTGATCACGGAGATTTC  1980
 581   K  L  A  P  E  E  A  G  G  T  P  V  I  T  E  I  F         601
1981 AGCCTGGGGTGGAACCCGCTTCCGAGATACAGCAGTCTGGTTGCCAAGGTCCAAAGACCTT 2040
 601   S  L  G  G  T  R  F  R  D  T  A  V  W  L  P  R  S  K  D  L  621
2041 AAAAAACCTGGAGCTAGAAAGCAGTAGACTGGAGGCTTCTACAGACTGTAGGATTCAAGG 2100
 621   K  K  P  G  A  R  K  Q                                      629
2101 TGATATTTGCAGACTGGCTTTATGAGAGACAACACTGATCTACTAGGGGCTGGACCCTAC 2160
 629                                                                629
2161 ATTGGTTGCCAGGCTTGTGTGTGAATCACCCCTAGGAGGAAAAAACCTACTATCAAACCT 2220
 629                                                                629
2221 GAAGAGCAGGCCTAAGAGTACTTTGAGCTTCTAG                             2254
 629
```

FIG. 3A-1

DNASIS Translation Editor (FTF-B)

```
  1 GAACAGCCGGGAGGCGACAGCTACCGCTTCAGAGGAGGCGGAGGAGGAGGAAG                                    60
 61 GGGAGGAGGGCGAGGCGGGAGGTGCAGGAGGACCCTCGCCATGGTTCCACGGCCTAGA                              120
121 GTGGCGGAAGATACCGGCCTGGTGCCAAACTGGCCTACTGCTGCTTCCTGTGCCTCCATG                            180
                                                                M                            1
181 GCTGAGGACTGGCTGGACTGCCCGGCCCTGGGCTGGAAGCGCGAAGTCTTT                                    240
      A  E  D  W  L  D  C  P  A  L  G  P  W  K  R  E  V  F                                 21
241 CGCAAGTCAGGGGCCACCTGTGAGCTCAGACGCTCAGATACCCACAGGAGAC                                   300
      R  K  S  G  A  T  C  E  L  R  R  S  D  T  Y  Y  Q                                     41
301 AGGATCCGAAGCAAAGTTGAGCTGACTCGATATCTGGGCCCTGCGTGATCTCACCCTC                             360
      R  I  R  S  K  V  E  L  T  R  Y  L  G  P  A  C  D  L  T  L                            61
361 TTTGACTTCAAACAAGGCATCTTGTGCTATCCCAAGGCCCCAAGGACTCGGAAACGTCAGGTT                         420
      F  D  F  K  Q  G  I  L  C  Y  P  K  A  H  P  V                                         81
421 GCCAGCAAGAAGCAAAGAAAGCCTTCAAGGCCAGCCAGCCCGAGGATGAGAACTGTGAGAACT                         480
      A  S  K  K  R  K  P  S  R  P  A  K  T  R  Q                                           101
481 CCCCAGAGTGGTGAGGTCAGGAAGGAGGCCCCGAGGATGAGAACTGTGAGAATCAGCTTCTCA                         540
      P  Q  S  G  E  V  R  K  E  A  P  R  D  E  T  K  A  D  T                               121
541 ACAGCCCCAGCTTCATTCCCTGCTCCTGGAATCTGTGAGAACTGTCAGACACAGAGA                              600
      T  A  P  S  F  I  P  C  S  C  E  N  C  G  H  S  E  A  R                                141
601 GGGGATGGCACCCAAAGGCAGCGGCTCAAAAGTTAAGCGTGTGGGCTGTGGAGTGTGCAGCC                          660
      G  D  G  T  Q  R  Q  R  L  K  S  K  V  G  C  E  C  A  A                               161
661 ATTGCCTTCAACCGGGAACAGAGAATGTTAAGCGTGTGGGCTGTGGAGTGTGCAGCC                               720
      I  A  F  N  R  E  Q  R  M  F  K  R  V  G  E  C  A  A                                  181
721 TGCCAGGTAACAGAAGACTGTGTTCTGCAAGTGTGAACGCTGCCCTGCCCTGCCCCATGAT                            780
      C  Q  V  T  E  D  C  V  L  Q  V  C  E  R  C  P  A  C  P  H  D                         201
781 GTGGCATCGGGGCTGTTCTGCAAGTGTGAACGCTGCCCTGCCCCGGATTGTGCCATTGCCC                            840
      V  A  S  G  L  F  C  K  C  E  R  C  L  R  I  V  H  C                                  221
841 AGCCGAGGGTGTGAGTATGCCGGGGCTGTCAGACCCAAGAGGATTGTGCCATTGCCC                                900
      S  R  G  V  R  C  T  Q  T  Q  E  D  C  H  C  P                                        241
```

FIG. 3A-2

DNASIS Translation Editor (FTF-B)

```
901  ATCTGCCTTCGCCCTCCCCGCCCTGGTCTCTCAGGCGCCAGTGTGGAAATGTGTCCAGCGACGT  960
241   I  C  L  R  P  P  R  P  G  L  R  Q  W  K  C  V  Q  R  R   261
961  TGCCTACGGCACCTTGCTCACCGTCTGCGTCGCCGTCATCAGAGATGTCAGCGACGCACT   1020
261   C  L  Y  G  T  L  L  T  V  C  V  A  V  I  R  D  V  S  D  A  T   281
1021 CCCCTGGCTGTGGCTCCCCAACTGGTAAACATGCCCGCCAAGGGAGGCTGTGACTCC     1080
281   P  L  A  V  A  P  T  G  K  H  A  R  K  G  G  C  D  S     301
1081 AAGATGGCTGCCAGAGCGGCGCCCAGCCCTGCCTCCACCCCATCACAG             1140
301   K  M  A  A  R  R  P  G  A  Q  P  L  P  P  P  S  Q              321
1141 TCCCCAGAGAGCCACAGAGCCGCACCCCAGAGCCCTGGCCCCCTCGCCAGTTC         1200
321   S  P  E  P  T  E  P  H  P  R  A  L  A  P  S  P  A  E  F        341
1201 ATCTATTACTGTGTAGAGGACTAAAAGCGGCTGCTGCCCAGTGTCTGGTCAGAG          1260
341   I  Y  Y  C  V  D  E  D  L  K  R  L  L  P  S  V  W  S  E         361
1261 TCTGAGGATGGGGCAGGATCGCCCCACCTTGAAGCCCACCTTACCGTCGTTGGCTACCGTGCC  1320
361   S  E  D  G  A  G  S  P  P  T  L  K  P  T  L  P  Y  R  R  K  P  S  S  A   381
1321 CGACGGCACCATCTTGCCTACCTTGAAGCCCACCTTGGCTACACGCACAGCCCAACCA      1380
381   R  R  H  H  L  A  Y  L  E  A  H  L  A  T  R  T  A  Q  P        401
1381 GACCATACCCAGCTCCAACGAAGCAGGTGTGCTTTGTGCTGTGCCCCCGCCT          1440
401   D  H  T  Q  L  Q  R  S  R  C  A  L  C  L  C  P  P           421
1441 GGCACTGACCTTGTGTTTTACGGAAGCAGTCCTGTGCAGGTGCCGGCCCT             1500
421   G  T  D  L  V  F  L  R  E  Q  V  P  G  P               441
1501 GTTGCAGCTTCCACAGAAGCCCTGTTGCAGGAGCCTCTGCCTGAGTTGGGTT            1560
441   V  A  A  S  T  E  A  L  L  Q  E  P  L  S  W  V             461
1561 GTGGCCCTTACCCCAGGTGAAGCAAGAGAAGGCGGATACCAGGTGGACACCAGGC         1620
461   V  A  L  T  P  Q  V  K  Q  E  K  A  D  T  Q  D  E  W  T  P  G        481
1621 ACAGCTGTCCTGACTTCTCCCGTATTGGTGTCCCTGCCTAGCAAGGCAGTAGACCCA      1680
481   T  A  V  L  T  S  P  V  L  V  P  C  P  S  K  A  V  D  P        501
1681 GGCCCTGCCTTCTGTGAAGCAAGAGCCACCTGAAGCAAGAGGAGGAAGAACAAG        1740
501   G  L  P  S  V  K  Q  E  P  D  P  P  E  E  D  K  E  N  K        521
1741 GATGATTCTGCCTCCAAAATTGGCCCCAGAGGAGAAGAGGCAGGAGGGCTGCACACCCGTG  1800
521   D  D  S  A  S  K  L  A  P  E  E  E  A  G  G  A  T  P  V        541
```

FIG. 3A-3

```
DNASIS  Translation Editor    (FTF-B)
1801 ATCACGGAGATTTCAGCCTGGGTGGAACCCGCTTCCGAGATACAGCAGTCTGGTTGCCA 1860
 541  I  T  E  I  F  S  L  G  G  T  R  F  R  D  T  A  V  W  L  P    561
1861 AGGTCCAAAGACCTTAAAAACCTGGAGCTAGAAAGCACTGGAGACTTCTACAGA 1920
 561  R  S  K  D  L  K  K  P  G  A  R  K  Q                          574
1921 CTGTAGGATTCAAGGTGATATTTGCAGACTGGCTTTATGAGAGACAACACTGATCTACTA 1980
 574                                                                 574
1981 GGGGCTGGACCCTACATTGGTTGCCAGGGCTTGTGTGTGAATCACCCCTAGGAGGAAAAA 2040
 574                                                                 574
2041 CCTACTATCAAACCTGAAGAGCAGGCCTAAGAGTACTTTGAGCTTCTAG 2089
 574                                                             574
```

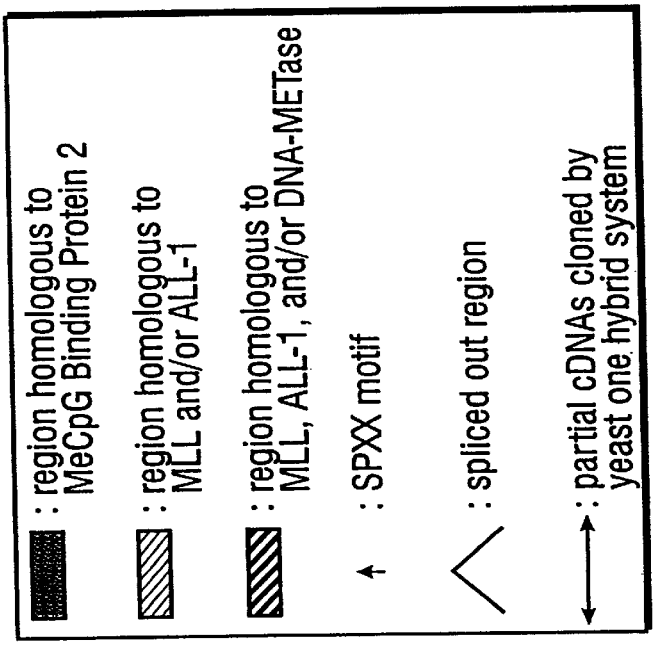

- ▨ : region homologous to MeCpG Binding Protein 2
- ▧ : region homologous to MLL and/or ALL-1
- ▨ : region homologous to MLL, ALL-1, and/or DNA-METase
- ↑ : SPXX motif
- ⋀ : spliced out region
- ↔ : partial cDNAs cloned by yeast one hybrid system

FIG. 4

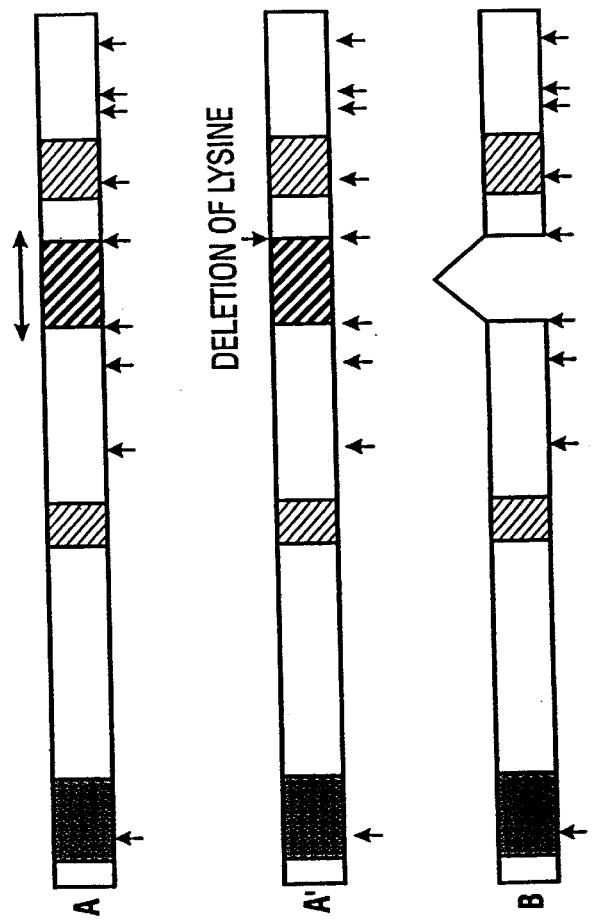

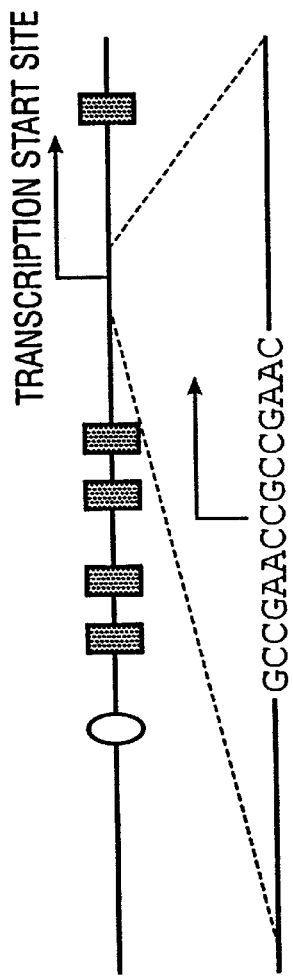

MAEDWLDCPALGPGPWKRREVFRKSGATCGRSDTYYQSPTGDRIRSKVELT
RYLGPACDLTLFDFKQGILCYPAPKAHPVAVASKKKRKKPSRPAKTRKRQV
GPQSGEVRKEAPRDETKADTDTAPASFPAPGCCENCGISFSGDGTQRQRL
KTLCKDCRAQRIAFNREQRMFKRVGGECAACQVTEDCGACSTCLLQLPH
DVASGLFCKCERRCLRIVERSRGGVCRGCQTQEDCGHCPICLRPPRPG
LRRQWKCVQRRCLRHLAHRLRRRHQRCQRRTPLAVAPPTGKHARRKGGCD
SKMAARRRPGAQPLPPPPSQSPEPTEPHPRALAPSPPAEFIYYCVDEDE
LQPYTNRRQNRKCGACAACLRRMDCGRCDFCCDKPKFGGSNQKRQKCRWR
QCLQFAMKRLLPSVWSESEDGAGSPPPYRRRKRPSSARRHHLGPTLKPTL
ATRTAQPDHTQAPTKQEAGGGFVLPPPGTDLVFLREGASSPVQVPGPVAA
STEALLQEAQCSGLSWVALPQVKQEKADTQDEWTPGTAVLTSPVLVPGC
PSKAVDPGLPSVKQEPPDPEEDKEENKDDSASKLAPEEEAGGAGTPVITE
IFSLGGTRFRDTAVWLPRSKDLKKPGARKQ

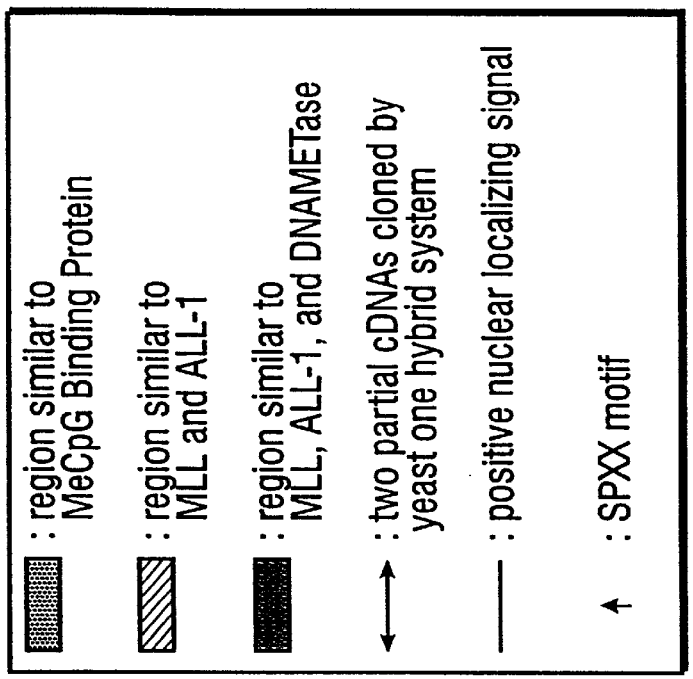
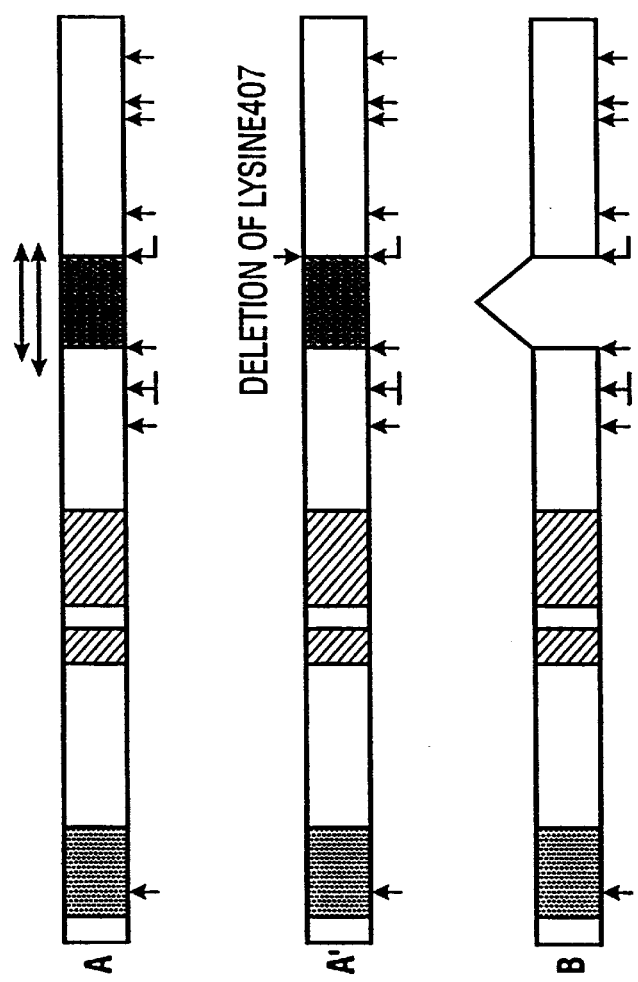
FIG. 5C

NUCLEIC ACIDS ENCODING REGULATORS OF FGF-2 TRANSCRIPTION (RFT) AND VARIANTS THEREOF

FIELD OF THE INVENTION

This invention relates generally to the field of regulation of transcription and more specifically to genes encoding polypeptide regulators of fibroblast growth factor-2 (FGF-2) expression.

BACKGROUND OF THE INVENTION

Many transcription factors are sequence-specific DNA-binding proteins. In general, transcription factors contain two functional domains, one for DNA-binding and one for transcriptional activation or suppression. These functions often reside within structural domains that retain their function when removed form their natural context. The DNA-binding domains of transcription factors falls into several structural families based on their primary amino acid sequence. Examples of families include the helix-tuml-helix, zinc finger, leucine zipper, and helix-loop helix proteins.

Helix-turn-helix proteins have a protein helix which lies across the major grove of the DNA helix and makes contact with exposed base pairs. These proteins contain a second helix that lies across the first and contacts other proteins in the transcription apparatus. Zinc finger proteins have a repeated motif of cysteine and histidine that are thought to fold up into a three-dimensional structure coordinated by a zinc ion. Examples of zinc finger proteins are Sp1, and steroid receptor proteins. Leucine zipper proteins have repeats of four of five leucine residues precisely seven amino acids apart which provide hydrophobic faces though which the proteins can form dimers. Adjacent to the leucine zipper is a domain enriched for positively charged amino acids, arginine and lysine. This DNA-binding domain is amino terminal to the leucine zipper. Examples of leucine zippers are c-fos and c-jun. Helix-loop-helix proteins are similar to the leucine zipper family as they bind DNA as homo- or heterodimers. Helix-loop-helix proteins also have a positively charged domain that recognizes the DNA. Examples of helix-loop-helix proteins are Myo1) and c-myc. These categories of transcription factors are not absolute; there are many transcription factors that do not fall into any of these categories.

The regions of transcription factors required for regulating transcription once the DNA-binding domain brings the factor in close contact with the DNA are called "activation domains" or "suppression domains." These domains are less well characterized than the DNA-binding domains. In some proteins, the activation domain has a net negative charge. However, many potent transcription factors lack acidic regions; the biochemical characteristics of these proteins is not yet understood. At present, most theories of how proteins interact to regulate transcription are highly speculative (for review of transcription factors see: DNA: A Short Course, second edition, J. D. Watson et al. (eds), W. H. Freeman and Co., N.Y., 1992, pp. 161–168).

Fibroblast growth factors are a family of related proteins, most of which initiate fibroblast proliferation. The FGF family includes nine members (FGF1–9), all of which are characterized by an internal 120 amino acid sequence that allows for growth factor binding to cell surface receptors (e.g., Coulier, F., et al., 1994, *Prog. Growith acclor Res.* 5:1). Considerable species crossreactivity has been reported for FGF 1–7 and 9 (e.g., Mathieu, M., et al., 1995, *Ann. Rev.* *Biochen.* 58:575). FGF-2 (or basic FGF) induces proliferation of fibroblasts, endotlhelial cells, condrocytes, smooth muscle, and melanocytes. It has also been found to induce adipocyte differentiation, stimulate astrocyte migration, and prolong neuron survival (Burgess, W. H., and Maciag, T., 1989, *Ann. Rev. Biochem.* 58:575). It has been proposed that FGF-2 plays a role in angiogenesis (reviewed in: Slavin, *J Cell Biol. Int.* 19:431–444), wound healing, tissue repair, embryonic development, differentiation, neuronal function and neuronal degeneration. Additionally FGF-2 may participate in the production of a variety of pathological conditions resulting from excessive cell proliferation and excessive angiogenesis. For example, FGF-2 is associated with pituitary lactotropli tumorigenesis (Schwcppe, R. E., et al., 1997, *J. Biol. Chem.* 272:30852–9), melanoma (Halaban, R., 1996, *Semin. Oncol.* 23: 673–81)), and astrocytoma (Morrison, R. S., et al., 1994, *J Neuroncol.* 18:207–16).

Wound healing is a complex and protracted process of tissue repair and remodeling involving many different cell types that require a finely tuned control of various biochemical reaction cascades to balance degradative and regenerative processes. Among other things the process comprises the migration of different cell types into the wound region, growth stimulation of epithelial cells and fibroblasts, formation of new blood vessels, and the generation of a new extracellular matrix. At all phases correct functioning critically depends on the biological activities of various cytokines, including chemokines, FGF, FGF-1, FGF-2, IGF, PDGF, and TGF. Animal experiments and clinical experience have demonstrated that the topical administration of various cytokines, including FGF-2, FGF, KGF, PDGF, TGF-β, either alone or in combination, considerably accelerates wound healing.

SUMMARY OF THE INVENTION

The present invention is based on the discovery of genes that regulate expression of FGF-2. These genes are termed "regulators of FGF-2 transcription (RFT1)".

In a first embodiment, the invention provides a substantially pure regulator of fibroblast growth factor-2 transcription (RFT)-A polypeptide. RFT-A is a negative regulator of the transcription of FGF-2. Substantially pure variants of RFT-A polypeptide, termed RFT-A' and RFT-B, are also provided. RFT-A' is a splice variant of RFT-A, having a deletion of a lysine at position 407 from the amino-terminus. RFT-A' is a positive regulator of FGF-2 transcription. RFT-B is a splice variant of RFT-A, missing 56 amino acids which are deleted form positions 351–406 of REFT-A. RFT-B is also a positive regulator of the transcription of FGF-2. Also included in the invention are isolated polynucleotides encoding RFT-A, RFT-A' and RFT-B polypeptide. In another aspect, antibodies that bind to RFT-A, RFT-A', or RFT-B polypeptides are disclosed.

In another embodiment, the invention provides a method for diagnosis or prognosis of a subject having or at risk of having a disorder associated with FGF-2. The method includes contacting a target cellular component containing FGF-2 in a specimen from the subject with an agent which detects RFT-A (SEQ ID NO:2) or at least one variant thereof; determining the level of RFT-A or at least one variant thereof and comparing the level to a normal specimen, thereby providing a diagnosis or prognosis of the subject. The target cellular component can be nucleic acid or protein, and the agent can be a nucleic acid probe or an antibody, respectively, for example.

In yet another embodiment, the invention provides a method of treating a cell proliferative disorder associated with FGF-2. The method includes administering to a subject with the disorder, a therapeutically effective amount of an agent which modulates FGF-2 expression. Such agents include a polynucleotide encoding RFT-A polypeptide.

The invention also includes a diagnostic kit useful for the detection of a target cellular component indicative of a disorder associated with FGF-2. The kit includes a carrier means containing one or more containers comprising a first container containing a probe for detection of RFT-A nucleic acid or a probe for detection of RFT-A polypeptide.

In another embodiment, the invention provides a method for identifying a compound that affects RFT-A polypeptide (SEQ ID NO:2) or a variant thereof. The method includes incubating components comprising the compound, RFT-A polypeptide or a variant thereof, and a nucleic acid sequence comprising a 5'-GCCGAAC-3' motif operably linked to a reporter gene, under conditions sufficient to allow the components to interact; and determining the effect of the compound on expression of the reporter gene.

In another embodiment, the invention provides a method for identifying a cellular protein that binds to RFT-A polypeptide or a variant thereof The method includes incubating components comprising at least one cellular protein and RFT-A polypeptide or a variant thereof, under conditions sufficient to allow the components to interact; separating a complex of RFT-A or a variant thereof, and a putative binding protein from unbound RFT-A or variant thereof, and isolating the protein.

In another embodiment, the invention provides a method for accelerating angiogenesis or wound healing in a subject. The method includes administering to the subject an effective amount of an agent for increasing expression of FGF-2, thereby accelerating angiogenesis or wound healing. In one aspect, the invention provides pharmaceutical compositions useful for treatment of FGF-2 disorders or accelerating wound healing or angiogenesis including the polypeptide of SEQ ID NO:2, SEQ ID NO:4, or SEQ ID NO:6 (RFT-A, RFT-A' or RFT-B, respectively) in a pharmaceutically acceptable carrier.

In another embodiment, transgenic nonhuman animals having a transgene disrupting or interfering with expression of RFT-A are described. A method for producing transgenic nonhuman animals having a phenotype characterized by increased expression of FGF-2 as compared to wild type animals is also provided.

BRIEF DESCRIPTION OF THE DRAWINGS

Figures 1A-2, 1B-1:
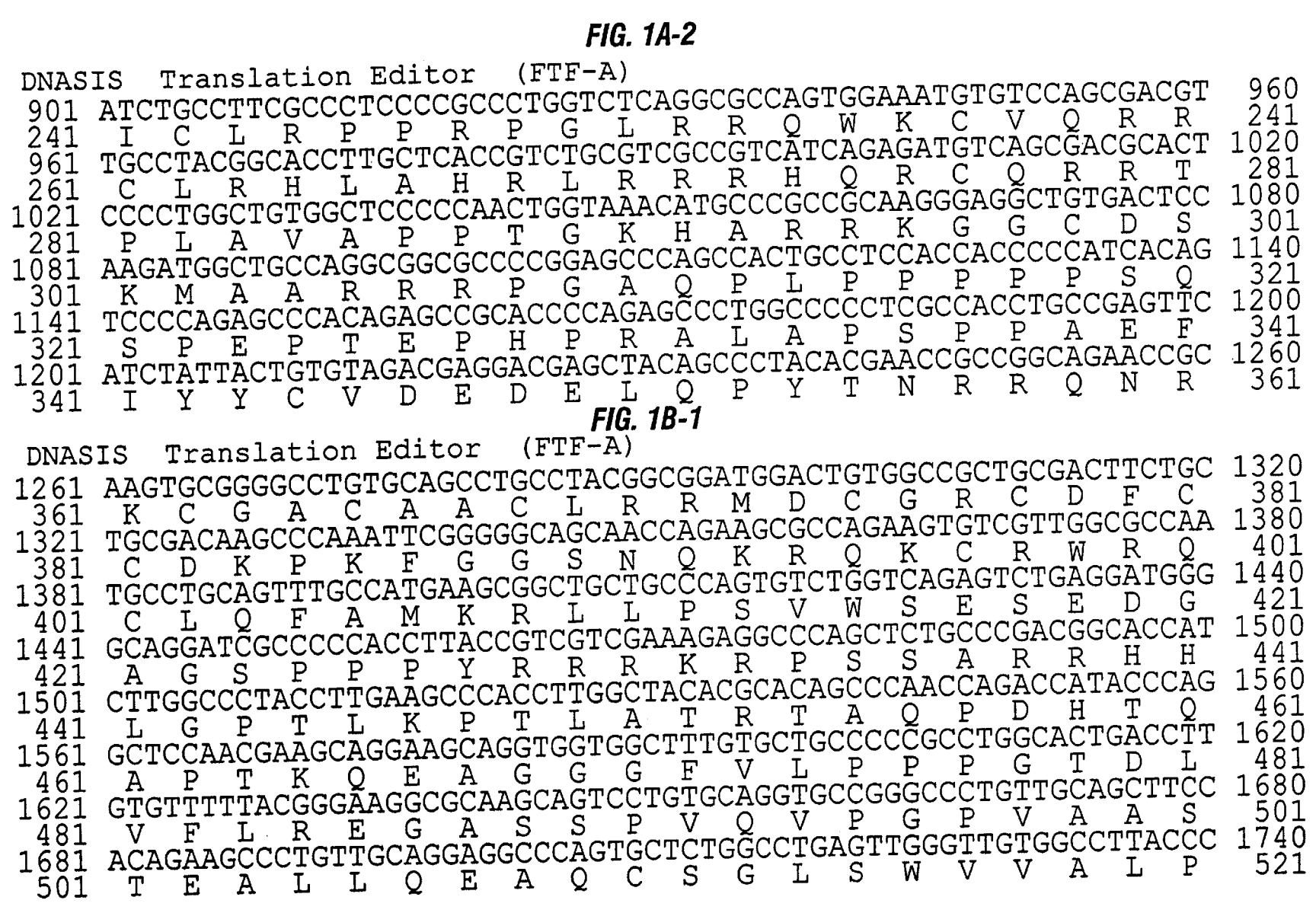

FIGS. 1A and 1B are the nucleotide (SEQ ID NO:1) and amino acid sequence (SEQ ID NO:2) of RFT-A.

FIGS. 2A and 2B are the nucleotide (SEQ ID NO:3) and amino acid sequence (SEQ ID NO:4) of RFT-A'.

FIGS. 3A and 3B are the nucleotide (SEQ ID NO:5) and amino acid sequence (SEQ ID NO:6) of RFT-B.

FIG. 4 is a schematic diagram showing the regions of homology in the RFT-A, RFT-A' and RFT-B sequences with other genes.

FIGS. 5A–5C show the molecular cloning of the RFT gene. FIG. 5A (SEQ ID NO:78) is a schematic presentation of the human FGF-2 promoter and its transcription start site. ""gccgaac" sequences are shown. FIG. 5B (SEQ ID NO:2) shows a deduced amino acid sequence of the RFT gene. Underlined regions were cloned by the yeast one hybrid system. Cysteines with asterisks are putative zinc fingers. K in italics indicates deleted lysine at 407 for RFT-A'. Bold letters show the domain spliced out for RFT-B. FIG. 5C shows a schematic presentation of RFT-A, RFT-A', and RFT-B.

FIG. 6A shows a design of ribonuclease protection assay (RPA) for detection of each form of the endogenous RFT gene. FIG. 6B shows RPA for each form of the RFT gene. The size is shown by the DNA marker (bp). (RNA:RNA) bands migrate slower than double stranded DNA markers.

DESCRIPTION OF THE PREFERRED EMBODIMENTS

Figure 6B:
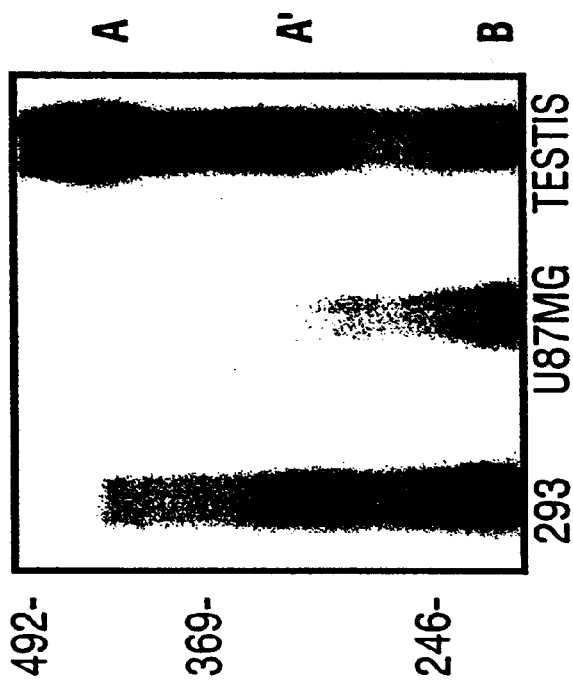
FIGS. 6A and 6B show the biological activity of the RFT gene.

The present invention provides genes encoding transcriptional regulators of FGF-2 expression, including both negative regulators and positive regulators. FGF-2 is a pleotropic growth factor, therefore, the transcriptional regulatory molecules of the invention are useful in the diagnosis, prognosis and treatment of a variety of disorders.

POLYNUCLEOTIDES AND POLYPEPTIDES

In a first embodiment, the invention provides substantially purified regulator of fibroblast growth factor-2 (FGF-2) transcription (RFT) polypeptides. The term "substantially purified" as used herein refers to a polypeptide which is substantially free of other proteins, lipids, carbohydrates or other materials with which it is naturally associated. One skilled in the art can purify RFT polypeptides using standard techniques for protein purification. The substantially pure polypeptide will yield a single major band on a non-reducing polyacrylamide gel. The purity of the RFH polypeptide can also be determined by amino-terminal amino acid sequence analysis.

A "regulator of fibroblast growth factor-2 transcription" is a molecule which modulates the level of transcription from a FGF-2 promoter as compared to the level of transcription from the FGF-2 promoter in the absence of the molecule. A "inegative regulator of FGF-2 transcription" is a molecule which decreases the level of transcription from a FGF-2 promoter as compared to the level of transcription from the FGF-2 promoter in the absence of the molecule, whereas a "positive regulator of FGF-2 transcription" is a molecule which increases the level of transcription from a FGF-2 promoter as compared to the level of transcription from the FGF-2 promoter in the absence of the molecule. The invention provides substantially purified RFT-A, which is a negative regulator of FGF-2 transcription. Preferably, RFT-A has an amino acid sequence set forth in SEQ ID NO:2.

The invention provides variants of RFT-A including, but not limited to, RFT-A' and RFT-B. A "variant" contains a modified RFT-A protein sequence such that the variant affects transcription of FGF-2. While not wanting to be bound by a particular theory, it is believed that RFT-A' and RFT-B dimerize with RFT-A and regulate transcription by removing RFT-A as a negative regulator of transcription (e.g., RFT-A/RFT-A' or RFT-A/RFT-B). Alternatively, RFT-A' and RFT-B may directly compete with RFT-A for binding to the FGF-2 consensus sequence, GCCGAAC.

In one aspect, the invention provides substantially purified RFT-A', a positive regulator of FGF-2 transcription. RFT-A' is a splice variant of RFT-A, with the lysine at position 407 of the RFT-A sequence has been deleted. Preferably, RFT-A' has an amino acid sequence as set forth in SEQ ID NO:4. RFT-A' is a positive regulator of FGF-2 transcription.

In another aspect, the invention provides substantially purified RFT-B. RFT-B is a splice variant of RFT-A, wherein the 56 amino acids located from position 351 to position 406 in RFT-A are deleted. RFT-B is a positive regulator of FGF-2 transcription. Without being bound by theory, RFT-B may act directly on the FGF-2 promoter, or it may act to regulate the negative activation of FGF-2 of RFT-A itself. Preferably, RFT-B has an amino acid sequence as set forth in SEQ ID NO:6.

The invention includes functional RFT-A, RFT-A', and RFT-B polypeptides as well as functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of RFT polypeptide," refers to all fragments of a RFT that retain RFT activity, e.g., the ability to positively or negatively regulate transcription from an FGF-2 promoter or bind to an antibody that binds to RFT. Biologically functional fragments, for example, can vary in size from a polypeptide fragment as small as an epitope capable of binding an antibody molecule to a large polypeptide capable of participating in the characteristic induction or programming of phenotypic changes within a cell. For example, functional fragments of RFT-A can still bind to the FGF-2 promoter consensus sequence, GCCGAAC.

Minor modifications of the RFT-A, RFT-A' or RFT-B primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the RFT still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids required for RFT activity. Alternatively, modified RFT polypeptides may be dominant negative, as described further below.

RFT-A polypeptide includes amino acid sequences substantially the same as the sequence set forth in SEQ ID NO:2; RFT-A' polypeptide includes amino acid sequences substantially the same as the sequence set forth in SEQ ID NO:4; and RFT-B polypeptide includes amino acid sequences substantially the same as the sequence set forth in SEQ ID NO:6. The term "substantially the same" refers to amino acid sequences that retain the activity of RFET as described herein, e.g., the ability to modulate transcription from an FGF-2 promoter. The RFT polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides polynucleotides encoding the RFT polypeptides described herein. These polynucleotides include DNA, cDNA and RNA sequences which encode RFT polypeptides. It is understood that all polynucleotides encoding RFT polypeptides are also included herein, as long as they encode a polypeptide with RFT activity. Such polynucleotides include naturally occurring, synthetic, and intentionally manipulated polynucleotides. For example, RFT polynucleotide may be subjected to site-directed mutagenesis. The polynucleotide sequence for RFT also includes antisense sequences, and sequences encoding dominant negative forms of RFT. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of RFT polypeptide encoded by the nucleotide sequence is functionally unchanged.

Specifically disclosed herein is a polynucleotide sequence encoding the RFT-A polypeptide. Preferably, the RFT-A nucleotide sequence is SEQ ID NO:1 having 2257 nucleotides and encoding a polypeptide of 630 amino acids. The polynucleotide encoding the RFT-A' polypeptide is also disclosed. Preferably, the RFT-A' nucleotide sequence is SEQ ID NO:3 having 2254 nucleotides and encoding a polypeptide of 629 amino acids. The polynucleotide encoding the RFT-B polypeptide is also disclosed. Preferably the RFT-B nucleotide sequence is SEQ ID NO:5 having 2089 nucleotides and encoding a polypeptide of 574 amino acids.

The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaiyote or eukaryote, or which exists as a separate molecule (eg., a cDNA) independent of other sequences. The nucleotides of the invention can be ribonucleotides, deoxyribonucleotides, or modified forms of either nulcleotide. The term includes single and double forms of DNA.

The polynucleotide encoding RFT-A includes SEQ ID NO:1, dominant negative forms of RFT-A, and nucleic acid sequences complementary to SEQ ID NO:1. The polynucleotide encoding RFT-A' includes SEQ ID NO:3, dominant negative forms of RFT-A', and nucleic acid sequences complementary to SEQ ID NO:3. The polynucleotide encoding RFT-B includes SEQ ID NO:5, dominant negative forms of RFT-B, and nucleic acid sequences complementary to SEQ ID NO:5. A complementary sequence may include an antisense nucleotide. When the sequence is RNA, the deoxynucleotides A, G, C, and T of SEQ ID NO:1, SEQ ID NO:3, and SEQ ID NO:5 are replaced by ribonucleotides A, G, C, and U, respectively. Also included in the invention are (1) fragments of the above-described nucleic acid sequences and are at least about 15 bases in length, which is sufficient to permit the fragment to selectively hybridize to DNA that encodes the protein of SEQ ID NO:2 under physiological conditions or a close family member of RFT-A, (2) fragments of the above-described nucleic acid sequences and are at least about 15 bases in length, which is sufficient to permit the fragment to selectively hybridize to DNA that encodes the protein of SEQ ID NO:4 under physiological conditions or a close family member of RFTT-A', and (3) fragments of the above-described nucleic acid sequences and are at least about 15 bases in length, which is sufficient to permit the fragment to selectively hybridize to DNA that encodes the protein of SEQ ID NO:6 under physiological conditions or a close family member of RFT-13. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows:2×SSC/0.1% SDS at about room temperature (hybridization conditions); 0.2 ×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences encoding RFT-A, RFT-A', or RFT-B can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the RFT polynucleotide sequences may be inserted into an expression vector. The term "expression vector" refers to a plasmid, virus or other vehicle known in the art that has been manipulated by insertion or incorporation of the RFT genetic sequences. Polynucleotide sequence which encode RFT can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the collect reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3 ' regions of the gene. Both constitutive and inducible promoters, are included in the invention (see e.g., Bitter et al., 1987, *Methods in Enzymology* 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding RFT may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., 1987, *Gene* 56:125), the pMSXND expression vector for expression in mammalian cells (Lee and Nathans, 1988, *J. Biol. Chem.* 263:3521) and baculovirus-derived vectors for expression in insect cells. The DNA segment can be present in the vector operably linked to regulatory elements, for example, a promoter (e.g., T7, metallothionein I, or polyhedrin promoters).

In yeast, a number of vectors containing constitutive or inducible promoters may be used. For a review see, *Current Protocols in Molecular Biology*, Vol. 2, 1988, Ed. Ausubel et al, Greene Publish. Assoc. & Wiley Interscience, Ch. 13; Grant et al., 1987, "Expression and Secretion Vectors for Yeast," in *Methods in Enzymology*, Eds. Wu & Grossman, 31987, Acad. Press, N.Y., Vol. 153, pp.516–544; Glover, 1986, *DNA Cloning*, Vol. II, IRL Press, Wash., D.C., Ch. 3; and Bitter, 1987, "Heterologous Gene Expression in Yeast," *Methods in Enzymology*, Eds. Berger & Kimmel, Acad. Press, N.Y., Vol. 152, pp. 673–684; and *The Molecular Biology of the Yeast Saccharomyces*, 1982, Eds. Strathern et al., Cold Spring Harbor Press, Vols. I and II. A constitutive yeast promoter such as ADH or LEU2 or an inducible promoter such as GAL may be used ("Cloning in Yeast," Ch. 3, R. Rothstein In: *DNA Cloning* Vol. 11, A Practical Approach, Ed. D. M. Glover, 1986, IRL Press, Wash., D.C.). Alternatively, vectors may be used which promote integration of foreign nucleic acid sequences into the yeast chromosome.

Mammalian expression systems which utilize recombinant viruses or viral elements to direct expression may be engineered. For example, when using adenovirus expression vectors, the RFT coding sequence may be ligated to an adenovirus transcription/translation control complex, e.g., the late promoter and tripartite leader sequence. Alternatively, the vaccinia virus 7.5K promoter may be used.

(e.g., see, Mackett et al, 1982, *Proc. Natl. Acad. Sci. USA* 79:7415–7419; Mackett et al., 1984, *J. Virol.* 49:857–864, Panicali et al., 1982, *Proc. Natl. Acad. Sci. USA* 79:4927–4931). Of particular interest are vectors based on bovine papilloma virus which have the ability to replicate as extrachromosomal elements (Sarver, et al., 1981, *Mol Cell. Biol.* 1:486). Shortly after entry of this nucleic acid into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the RFT gene in host cells (Cone & Mulligan, 1984, *Proc. Natl. Acad. Sci. USA* 81:6349–6353). High level expression may also be achieved using inducible promoters, including, but not limited to, the metallothionein IIA promoter and heat shock promoters.

Polynucleotide sequences encoding RFT can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

For long-term, high-yield production of recombinant proteins, stable expression is preferred. Rather than using expression vectors which contain viral origins of replication, host cells can be transformed with RFT cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign nucleic acid, engineered cells may be allowed to grow for 1–2 days in an enriched media, and then are switched to a selective media. A number of selection systems may be used, including, but not limited to the herpes simplex virus thymidine kinase gene (Wigler, et al., 1977, *Cell* 11:223), hypoxanthine-guanine phosphoribosyltransferase gene (Szybalska & Szybalski, 1962, *Proc. Natl. Acad. Sci. USA* 48:2026), and the adenine phosphoribosyltransferase (Lowy, et al., 1980, *Cell* 22:817) genes can be employed in tk–, hgprt[31] or aprt[31] cells respectively. Additionally, antimetabolite resistance can be used as the basis of selection for dhfr, which confers resistance to methotrexate (Wigler, et al., 1980, *Natl. Acad. Sci. USA* 77:3567; O'Hare, et al., 1981, *Proc. Natl. Acad. Sci. USA* 78:1527); the gpt gene, which confers resistance to mycophenolic acid (Mulligan & Berg, 1981, *Proc. Natl. Acad Sci. USA* 78:2072; the neo gene, which confers resistance to the aminoglycoside G-418 (Colberre-Garapin, et al., 1981, *J. Mol. Biol.* 150:1); and the hygro gene, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); and ODC (ornithine decarboxylase) which confers resistance to the ornithine decarboxylase inhibitor, 2-(difluoromethyl)-DL-ornithine, DFMO (McConlogue L., 1987, In: *Current Communications in Molecular Biology*, Cold Spring Harbor Laboratory ed.).

By "transfoiation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which has been introduced, by means of recombinant DNA techniques, a DNA molecule encoding hSKCa3. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$, method using procedures well known in the art. Alternatively, $MgCl_2$ or RbC1 can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the RFT of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

ANTIBODIES

The RFT polypeptides of the invention can be used to produce antibodies which are immunoreactive or bind to epitopes of the RFT polypeptides. Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., Production of Polyclonal Antisera, in: *Immunochemical Protocols* (Manson, ed.), pages 1–5 (Humana Press 1992); Coligan et al., "Production of Polyclonal Antisera in Rabbits, Rats, Mice and Hamsters," in: *Current Protocols in Immunology*, section 2.4.1 (1992), which are hereby incorporated by reference.

The preparation of monoclonal antibodies likewise is conventional. See, for example, Kohler & Milstein, 1975, *Nature* 256:495; Coligan et al., sections 2.5.1–2.6.7; and Harlow et al., in: *Antibodies: a laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g. Coligan et al., sections 2.7.1–2.7.12 and sections 2.9.1–2.9.3; Barnes et all., Purification of Immunoglobulin G (IgG), in: *Methods in Molecular Biology*, Vol. 10, pages 79–104 (Humana Press 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., 1990, *Int. J. Cancer* 46:310, which are hereby incorporated by reference.

Alternatively, a therapeutically useful anti-RFT-A, anti-RFT-A', or anti-RFT-B antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., 1989, *Proc. Nat'l Acad. Sci. USA* 86:3833, which is hereby incorporated in its entirety by reference. Techniques for producing humanized monoclonal antibodies are described, for example, by Jones et al., 1986, *Nature* 321:522, Riechinann et al., 1988, *Nature* 332:323; Verhoeyen et al., 1998, *Science* 239:1534; Carter et al., 1992, *Proc. Nat'l Acad. Sci. USA* 89:4285; Sandhu, 1992, *Crit. Rev. Biotech.* 12:437; and Singer et al., 1993, *J. Immunol.* 150:2844, which are hereby incorporated by reference.

Antibodies of the invention also may be derived from human antibody fragments isolated from a combinatorial immunoglobulin library. See, for example, Barbas et al., 1991, in: *Methods: a Companion to Methods in Enzymology*, Vol. 2, page 119; Winter et al., 1994, *Ann. Rev. Immunol.* 12:433, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., 1994, *Nature Genet.* 7:13; Lonberg et al., 1994, *Nature* 368:856; and Taylor et al., 1994, *Int. Immunol.* 6:579, which are hereby incorporated by reference.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and No. 4,331,647, and references contained therein. These patents are hereby incorporated in their entireties by reference. See also Nisonhoff et al., 1960, *Arch. Biochem. Biophys.* 89:230, Porter, 1959, *Biochem. J.* 73:119; Edelman et al., 1967, *Methods in Enzymology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$, and $V_L$ chains. This association may be noncovalent, as described in Inbar et al., 1972, *Proc. Nat'l Acad. Sci. USA* 69:2659. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al, 1991, *Methods: a Companion to Methods in Enzymology*, Vol. 2, page 97; Bird et al, 1988, *Science* 242:423–426; Ladner et al., U.S. Pat. No. 4,946,778; Pack et al., 1993, *Bio/Technology* 11: 1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al. *Methods: a Companion to Methods in Enzymology*, Vol. 2, page 106 (1991).

Antibodies which bind to a RFT-A, RFT-A', and/or RFT-B polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the ail will know of various techniques common in the immunology ails for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

DETECTION OF AN FGF-2-ASSOCIATED DISORDER

The antibodies and polynueleotides of the invention can be used to detect or treat a FGF-2-associated disorder in a subject. The term "FGF-2-associated disorder" denotes cell proliferative as well as non-cell proliferative disorders where the cells involved in the disorder differ from the surrounding tissue or from unaffected cells in their expression of FGF-2. A "cell proliferative disorder" is any disorder in which the proliferative capabilities of the affected cells is different from the normal proliferative capabilities of unaffected cells. An example of a cell proliferative disorder is neoplasia. The term "FGF-2-associated disorder" denotes malignant as well as non-malignant disorders, where the cells involved in the disorder differ from the surrounding tissue or from unaffected cells in their expression of FGF-2. Malignant cells (i.e., cancer) develop as a result of a multistep process. Examples of disorders associated with increased expression of FGF-2 are low grade astrocytoma, anaplastic astrocytoma, glioma, glioblastoma, medulloblastoma, colon cancer, lung cancer, renal cancer, leukemia, testicular cancer, breast cancer, prostate cancer, endometrial cancer, and neuroblastoma. Preferably, the subject is a mammal, and more preferably, a human.

The invention can be used to determine the prognosis of a FGF-2-associated disorder. The "prognosis" is a forecast as to the probable outcome of an attack of a disease; the prospect as to recovery from a disorder as indicated by the nature and symptoms of the case. In addition, the invention may be used to identify or treat individuals who are "at risk" of developing a FGF-2-associated disorder. These individuals may be identified by a method of the invention for detecting the presence or absence of RFT-A, RFT-A', or RFT-B, or a variant thereof, or by any other diagnostic means, and/or may be treated by a method of the invention, prior to the actual onset of the clinical appearance of disorder. The "clinical appearance" can be any sign or symptom of the disorder.

For purposes of the invention, an antibody or nucleic acid probe specific for FGF-2 may be used to detect FGF-2 polypeptide (using antibody) or polynucleotide (using nucleic acid probe) in subject samples or "cellular components" such as biological fluids, cells, tissues, or cellular extracts, protein, nucleic acid such as DNA or RNA. Any specimen containing a detectable amount of antigen or polynucleotide can be used. Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample. Tissue samples may be obtained from such tissues as brain, urogenital, lung, renal, hematopoietic, breast, thymus, testis, ovarian, and uterine tissue.

The invention provides a method for detecting RFT-A, for example, which comprises contacting an RFT-A antibody or nucleic acid probe with a cell suspected of expressing FGF-2 and detecting binding to the antibody or nucleic acid probe. The antibody reactive with RFT-A or the nucleic acid probe is preferably labeled with a compound which allows detection of binding to RFT-A. A preferred sample of this invention is blood, brain tissue or tissue affected by a cell proliferative disorder (e.g., a tissue taken from a cancer patient).

The level of RFT-A in the subject cell can be compared with the level in a cell not affected by the disease process. The cell not affected by the disease process can be taken from the same subject, or can be from a control subject not affected by the disease process, or can be from a cell line, for example.

When the cell component is nucleic acid, it may be necessary to amplify the nucleic acid prior to binding with the RFT-A specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used. These methods can similarly be used to measure levels of RFT-A' or RFT-B.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the all will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

The monoclonal antibodies or polynucleotides of the invention can be used in vitro and in vivo to monitor the course of amelioration of a FGF-2-associated disease in a subject. The term "ameliorate" denotes a lessening of the detrimental effect of the FGF-2-associated disease in the subject receiving therapy. Thus, for example, by measuring the increase or decrease in the number of cells expressing FGF-2 or changes in the concentration of such FGF-2 present in various body fluids or tissues, it would be possible to determine whether a particular therapeutic regimen aimed at ameliorating the FGF-2-associated disease is effective.

THERAPEUTIC INTERVENTION

The present invention identifies a polynucleotide sequence that can be expressed in an altered manner as compared to expression in a normal cell, therefore it is possible to design appropriate therapeutic or diagnostic agents directed to this sequence. The antibodies and polynucleotides of the invention can be used to detect or to treat an FGF-2-associated disorder.

Essentially, any disorder which is etiologically linked to increased expression of FGF-2 could be considered susceptible to treatment with a FGF-2 negative regulator of transcription, such as RFT-A, and any disorder which is etiologically linked to decreased expression of FGF-2 could be considered susceptible to treatment with FGF-2 positive regulator of transcription, such as RFT-A' or RFT-B.

Detection of elevated levels of RFT expression is accomplished by hybridization of nucleic acids isolated from a cell of interest with a RFT polynucleotide of the invention. Northern Blot analysis, is utilized to quantitate expression of the RFT, such as to measure RFT-A transcripts. Other standard nucleic acid detection techniques will be known to those of skill in the art. Detection of elevated levels of RFT is also accomplished using the antibodies of the invention. RIA, is used to quantitate expression of the RFT, such as to measure protein concentration. All of these methods are described above.

Treatment can include modulation of FGF-2gene expression and FGF-2 activity by administration of a therapeutically effective amount of a reagent that modulates FGF-2, specifically by administering a RFT agent. The term "modulate" envisions the suppression of expression of FGF-2 when it is overexpressed, or augmentation of the expression of FGF-2 when it is underexpressed. The term "agent" as used herein describes any molecule, e.g., protein, nucleic acid, or pharmaceutical, with the capability of altering the expression of FGF-2 via a RFT molecule.

Candidate agents include nucleic acids encoding a RFT, or that interfere with expression of a RFT, such as an antisense nucleic acid. Candidate agents also encompass numerous chemical classes wherein the agent modulates RFT expression or activity.

Candidate agents also include antisense nucleic acid sequences. Antisense nucleic acids are DNA or RNA molecules that are complementary to at least a portion of a specific mRNA molecule (Weintraub, 1990, *Scientific American*, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target FGF-2-producing cell. The use of antisense methods to inhibit the in vitro translation of genes is well known in the art (Marcus-Sakura, 1988, Anal.Biochem., 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1(3):227; Helene, C., 1991, Anticancer Drug Design, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, J. Amer.Med. Assn., 260:3030). A major advantage of this approach is that, because they are sequence-specific, only mRNAs with particular sequences are inactivated.

There are two basic types of ribozymes namely, tetrathymena-type (Hasselhoff, 1988, Nature, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Where a disorder is associated with the decreased expression of FGF-2, nucleic acid sequences that encode RFT-A', RFT-B, or both RFT-A' and RFT-B can be used. Where a disorder is associated with the increased expression of FGF-2, nucleic acid sequences that interfere with the expression of FGF-2 can be used, specifically nucleic acid sequences that encode RFT-A can be used. This approach also utilizes, for example, antisense nucleic acid, ribozymes, or triplex agents to block transcription or translation of RFT-A' and/or RFT-B mRNA, either by masking that mRNA with an antisense nucleic acid or triplex agent, or by cleaving it with a ribozyme in disorders associated with increased FGF-2. In addition, this approach also utilizes, for example, antisense nucleic acid, ribozymes, or triplex agents to block transcription or translation of RFT-A mRNA, either by masking that mRNA with an antisense nucleic acid or triplex agent, or by cleaving it with a ribozyme in disorders associated with decreased FGF-2.

In one embodiment, in a cell proliferative disorder known in the art to be associated with increased FGF-2, such as low grade astrocytoma, anaplastic astrocytoma, glioma, glioblastoma, medulloblastoma colon cancer, lung cancer, renal cancer, leukemia, testicular cancer, breast cancer, prostate cancer, endometrial cancer, and neuroblastoma, an agent which modulates FGF-2 expression can be administered. Such disorders are associated with brain, urogenital, lung, renal, hematopoietic, breast, thymus, testis, ovarian, or uterine tissue. An agent which modulates FGF-2 expression includes a polynucleotide encoding the polypeptide of SEQ ID NO:2, or an antisense polynucleotide that binds to polynucleotide encoding SEQ ID NO:4 or SEQ ID NO:6.

FGF-2 is involved in wound healing and also known to be important in inducing neural progenitor cells to proliferate and differentiate into neurons, astrocytes, and oligodendrocytes. Therefore, in another embodiment, the invention provides treatment of a disorder associated with decreased FGF-2, such as a disturbance in wound healing or neuronal differentiation, an agent which modulates FGF-2 expression is administered. An agent which modulates FGF-2 expression includes a polynucleotide encoding the polypeptide of SEQ ID NO:4 or SEQ ID NO:6, or an agent that inhibits SEQ ID NO:2, such as an antisense polynucleotide that binds to polynucleotide encoding SEQ ID NO:2. Alternatively, a dominant negative form of RFT-A polypeptide could be administered.

In another embodiment, the invention provides a method of accelerating angiogenesis by administering an agent to increase FGF-2. An agent which modulates FGF-2 expression includes a polynucleotide encoding the polypeptide of SEQ ID NO:4 or SEQ ID NO:6, or an agent that inhibits SEQ ID NO:2, such as an antisense polynucleotide that binds to polynucleotide encoding SEQ ID NO:2. "Angiogenesis" is the processes leading to the generation of new blood vessels through sprouting from already existing blood vessels. Blood vessel growth occurs in the embryo and rarely in the adult with exceptions such as the female reproductive system, wound healing, and pathological processes such as cancer. Vascular expansion is the enlargement of small or occluded vessels which is frequently observed during the generation of collateral blood vessels. Under normal conditions all processes involving the new formation or the remodeling of existing new blood vessels, which normally is a self-limiting process, require the controlled and conceited growth of various specific cell types in order to avoid unwanted overgrowth. During tumor angiogenesis the directed sprouting of new blood vessels into the direction of the solid tumor mass can be observed. The formation of blood vessels is initiated and maintained by a variety of factors secreted either by the tumor cells themselves or by accessory cells. The list of angiogenically active protein factors includes: FGF-2, angiogenin, FGF, VEGF, TNF-alpha, TGF-beta, PD-ECGF, PDGF, IGF, and IL8.

The present invention also provides gene therapy for the treatment of disorders which are associated with FGF-2. Such therapy would achieve its therapeutic effect by introduction of a therapeutic polynucleotide into cells in vivo having the disorder or introducing the therapeutic polynucleotide into cells ex vivo and then reintroducing the cells into the subject. The "therapeutic polynucleotide" may be polynucleotide sequences encoding RFT-A, RFT-A', or RFT-B, or antisense polynucleotide specific for RFT-A, RFT-A', or RFT-B, designed to treat a FGF-2-associated disorder. Polynucleotides encoding dominant negative forms of RFT polypeptides of the invention are also included.

Delivery of the therapeutic polynucleotide can be achieved using, a recombinant expression vector such as a chimeric virus or a colloidal dispersion system. Especially preferred for therapeutic delivery of antisense sequences, or RFT polynucleotides, is the use of viral vectors or the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a RFT sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral geniome or attached to a viral envelope to allow target specific delivery of the retroviral vector containing the RFT polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.*, 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., 1988, *Biotechniques*, 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosplhatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

PHARMACEUTICAL COMPOSITIONS

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants. But even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, 1990, *Science*, 249:1527–1533, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., 1990, Goodman And Gilman's: *The Pharmacological Bases of Therapeutics*, 8th ed., Pergamon Press; and *Remington's Pharmaceutical Sciences*, 1990, 17th ed., Mack Publishing Co., Easton, Pa., each of which is herein incorporated by reference.

Thus the identification of RFT-A, RFT-A', and RFT-B provides a useful tool for diagnosis, prognosis and therapeutic strategies associated with expression of FGF-2.

KITS

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be an antibody or nucleic acid sequence specific for RFT-A, RFT-A', or RFT-B polypeptide or polynucleotide, or specific fragments of a RFT-A, RFT-A', or RFT-B polypeptide or polynucleotide. For example, oligonucleotide probes of the present invention can be included in a kit and used for examining the presence of SEQ ID NO:1, SEQ ID NO:3, SEQ ID NO:5, or a combination of SEQ ID NO:3 and SEQ ID NO:5 polynucleotide in a sample, as well as the quantitative (relative) degree of binding of the probe for determining the occurrence of specific strongly binding (hybridizing) sequences, thus indicating the likelihood for a subject having or predisposed to a disorder associated with FGF-2.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the RFT target sequence, this can be accomplished using oligonucleotide(s) that are primers for amplification. These oligonucleotide primers are based upon identification of the flanking regions contiguous with the target nucleotide sequence.

The kit may also comprise a container having antibodies which bind to RFT-A, RFT-A', or RFT-B polypeptide, or specific fragments thereof. Such antibodies can be used to distinguish the presence of a particular RFT or the level of expression of SEQ ID NO:2, SEQ ID NO:4, or SEQ ID NO:6, or a combination of SEQ ID NO:4 and SEQ ID NO:6, in a specimen. Where the kit utilizes antibodies to detect a RFT, these antibodies may be directly labeled. The kit may also comprise container having a reporter means, such as aviden or steptavin, bound to a reporter molecule such as an enzymatic, fluorescent, or radionucleotide label to identify the directly labeled antibody. Alternatively, the kit can utilizes antibodies that bind RFT-A, RFT-A', or RFT-B that are unlabeled. The kit may then also comprise container having a second antibody which binds to the antibody specific for RFT-A, RFT-A', or RFT-B. The second antibody can be directly labeled. The kit may also comprise a container having a reporter means, such as aviden or steptavin, bound to a reporter molecule such as an enzymatic, fluorescent, or radionucleotide label to identify the directly labeled second antibody. The kit can be used for the detection of a target cellular component associated with FGF. "Cellular components" include, but are not limited to, nucleic acid such as DNA or RNA, or proteins.

METHOD FOR IDENTIFYING COMPOUNDS THAT AFFECT RFT

The invention provides a method for identifying a compound which can modulate RFT activity. The method includes incubating RFT-A polypeptide or a recombinant cell expressing a RFT-A polypeptide or variant thereof, such as RFT-A' or RIUT-B, a nucleic acid sequence containing a 5'-GCCGAAC-3' motif operably linked to a reporter gene, and a test compound, Linder conditions sufficient to allow the components to interact, and measuring the effect of the compound on the expression of the reporter gene. The expression of the reporter gene in the sample can then be compared to the expression of the reporter gene in a control sample not incubated with the compound. Compounds that affect the interaction of RFT-A, RFT-A' and/or RFT-B with the 5'-GCCGAAC-3' motif operably linked to a reporter gene include peptides, polypeptides, pepidomimetics, chemical compounds and biological agents. Alternative assays include incubation of combinations of RFT polypeptides or cells expressing more than one RFT polypeptide (or more than one cell expressing different RFT polypeptides), e.g., RFT-A and RFT-A' or RFT-A and RFT-B.

"Incubating" includes conditions which allow contact between the test compound and RFT polypeptide. "Contacting" includes in solution and solid phase. The test compound may also be a combinatorial library for screening a plurality of compounds. A variety of other agents may be included in the screening assay. These include agents like salts, neutral proteins, e.g., albumin, detergents, etc that are used to facilitate optimal protein-protein binding and/or reduce non-specific or background interactions. Reagents that improve the efficiency of the assay, such as protease inhibitors, nuclease inhibitors, antimicrobial agents, etc., may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 hours will be sufficient.

Compounds that are nucleic acid in nature identified in the method of the invention can be further evaluated, detected, cloned, sequenced, and the like, either in solution of after binding to a solid support, by any method usually applied to the detection of a specific DNA, such as PCR, oligomer restriction (Saiki et al.,1985, *Bio/Technology*, 3:1008–1012), allele-specific oligonucleotide (ASO) probe analysis (Conner et al.,1983, *Proc. Natl. Acad. Sci. USA*, 80:278), oligonucleotide ligation assays (OLAs) (Landegren et al., 1988, *Science*, 241:1077), and the like. Molecular techniques for DNA analysis have been reviewed (Landegren et al., 1988, *Science*, 242:229–237).

Candidate compounds that affect RFT include chemical compounds. One class is organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A compound can affect reporter gene expression by either stimulating or inhibiting the expression of the reporter gene. A compound "inhibits" reporter gene expression if the level of transcripts or protein product produced from the reporter gene is decreased as compared with the level in the absence of the test compound. A compound "stimulates" reporter gene expression if the level of transcripts or protein product produced from the reporter gene is increased.

One of skill in the art can identify a number of reporter genes for use in the screening method of the invention. Examples of reporter genes of use with the invention are lacZ, luciferase, chloramplhenicol acetyltransferase, and green fluorescent protein.

The effect of the compound on the reporter gene transcription can be measured by assessing the expression of the reporter by methods well known in the art (e.g., Northern blots; EMSA). Alternatively or the production of protein product from the reporter gene can be measured by methods well known in the art (e.g., ELISA or RIA; Western blots; SDS-PAGE).

The invention further provides a method for identifying a cellular protein that binds to RFT-A polypeptide or a variant thereof, such as RFT-A' or RFT-B, by incubating at least one cellular protein and a RFT-A polypeptide or a variant thereof (e.g., RFT-A' or RFT-B) under conditions sufficient for the components to interact, and separating a complex of the RFT polypeptide and a putative binding protein from the unbound RFT, and isolating the protein (e.g., a 2-hybrid system).

In a preferred embodiment, an isolated cellular protein is utilized. However, partially purified proteins, fractions of cell extracts, whole cell extracts, or intact cells may be utilized with the method of the invention. "Incubating" includes conditions which allow contact between the cellular component and the RFT-A polypeptide, or RFT-A variant. The term "interact" includes in solution and solid phase, and includes any complex formation or binding of the cellular component to the RFT polypeptide. The term "interact also includes any enzymatic interaction wherein the cellular component performs a biochemical modification of the RFT polypeptide.

The complex of the cellular component with a RFT polypeptide can be separated from uncomplexed RFT polypeptide by conventional means, well known to one of skill in the art. The presence of cellular component bound to RFT-A can be accomplished by size separation, physical separation, or other standard methods. For example, nondeniaturing gel electrophoresis can be used to separate RFT-A complexed with a cellular component from uncomplexed RFT-A.

Once the complex has been isolated, the cellular component can be isolated and characterized by means well known in the art. For example, if the cellular component is a protein, the protein can be sequenced using methodology well known in the art. Polynucleotide encoding the protein can be produced using DNA synthesis technology. The polynucleotide can then be inserted into a vector Lising or molecular techniques well known in the art, and transformed into host cells using the techniques described above. Following transformation, large amounts of the protein may be isolated and purified in accordance with conventional ways. For example, lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

TRANSGENIC ANIMALS

In another embodiment, the present invention provides nonhuman transgenic animals having cells that have increased expression of FGF-2. Such transgenic animals represent a model system for the study of FGF-2 related disorders and the study of RFT based therapeutics.

The term "animal" here denotes all species except human. It also includes an individual animal in all stages of development, including embryonic and fetal stages. Farm animals (e.g., chickens, pigs, goats, sheep, cows, horses, rabbits and the like), rodents (such as mice), and domestic pets (e.g., cats and dogs) are included within the scope of the present invention. In a preferred embodiment the animal is a mouse or a rat.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring, in fact possess some or all of that information, then they, too, are transgenic animals.

It is highly preferred that the transgenic animals of the present invention be produced by introducing into single cell embryos DNA encoding a disrupted RFT-A, or a gene which disrupts or interferes with RFT-A expression, in a manner such that the polynucleotides are stably integrated into the DNA of germ line cells of the mature animal and inherited in normal Mendelian fashion. Alternatively, DNA encoding a disrupted RFT-A variant (e.g., A' or B) can be used to produce animals with decreased FGF-2 expression. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals are produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo* (Cold Spring Harbor Press 1986); Krimpenfort et al., 1991, *Bio/Technology* 9:86; Palmiter et al, 1985, *Cell* 41:343; Kraemer et al., *Genetic Manipulation of the Early Mammalian Embryo* (Cold Spring Harbor Laboratory Press 1985); Hammer et al., 1985, *Nature*, 315:680; Purcel et (al., 1986, *Science*, 244:1281; Wagner et al., U.S. Pat. No. 5,175,385; Krimpenfort et al., U.S. Pat. No. 5,175,384, the respective contents of which are incorporated by reference. In brief, the transgene encoding a disrupted RFT-A gene or a gene which disrupts or interferes with RFT-A expression is introduced into a zygote of an animal, preferably by microinjection. Zygotes are then transplanted into a pseudopregnant animal, and the animal is allowed to carry the embryos to term. Animals carrying the transgene are then identified by methods well known in the art, e.g., by dot blotting or Southern blotting.

The cDNA that encodes RFT-A or a variant thereof can be fused in proper reading frame under the transcriptional and translational control of a vector to produce a genetic construct that is then amplified, for example, by preparation in a bacterial vector, according to conventional methods. See, for example, the standard work: Sambrook et al., *Molecular Clonino: a Laboratory Manual* (Cold Spring Harbor Press 1989), the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or knocked out.

The transgene to be used in the practice of the subject invention is a DNA sequence comprising a modified RFT coding sequence. In a preferred embodiment, the endogenous RFT gene is disrupted by homologous targeting in embryonic stem cells. For example, the entire murine RFT gene may be deleted. Optionally, the RFT disruption or deletion may be accompanied by insertion of or replacement with other DNA sequences, such as a non-functional RFT-sequence. In other embodiments, the transgene comprises DNA antisense to the coding sequence for RFT-A or variant thereof. In another embodiment, the transgene comprises DNA encoding an antibody or receptor peptide sequence which is able to bind to RFT-A or a variant thereof. In another embodiment, embryonic stem cells are infected with a retrovirus containing a RFT-A gene. Where appropriate, DNA sequences that encode proteins having RFT activity but differ in nucleic acid sequence due to the degeneracy of the genetic code may also be used herein, as may truncated forms, allelic variants and interspecies homologues.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLES

Example 1

Materials and Methods

Yeast one hybrid screening, cloning whole cDNAs and Northern hybridization. Yeast one hybrid screening was conducted as described in the manufacturer's manual (Clontech) using human testis library (Tashiro K., et al., 1997, *Proc. Natl. Acid. Sci. USA* 94:7862–7867). The three "gccgaaccgccgaac" (SEQ ID NO. 8) tandem repeats were subcloned into pHisi plasmid as a reporter plasmid. Multiple tissue Northern blot membranes (Clontech) were hybridized with radiolabeled cDNAs identified through the yeast system. Whole cDNAs were also cloned by screening a human testis library (Clontech) with the radiolabeled cDNA probes. All cloned cDNA were sequenced by an automated sequencer.

Plasmid Construction, Cell Culture, DNA Transfection, Luciferase Assays, and B Galactosidase Assays.

To make His-tagged mammalian expression vectors of each form, polymerase chain reactions were performed and subcloned into pCDNA3 (In Vitrogen). All constructs were sequenced. As a reporter vector, pGL1.2F, 1.2 Kb of FGF-2 promoter (Shibata F., et al., 1991, *Growth Factors* 4:277–287) was subcloned into pGL-2- basic vector (Promega). U87MG (ATCC) and 293 cells (Graham, F. L., et al., 1977, *J. Gen. Virol.* 36:59–72) were incubated in the Dulbecco's modified Eagle medium with 10% fetal calf serum in a 5% $CO_2$ incubator. For DNA transfection, the calcium phosphate method was used for 293 cells and Superfectant (Qiagen) for U87MG. Briefly, 1×10⁵ cells were transfected with 0.9 mg of each expression vector or pCDNA3 as a control, 0.9 mg of pGL1.2F, and 0.2 mg of H-RASbGAL (Ishii, S., et al., 1985, *Science* 230:1378–1381) as an internal control. Luciferase assays and β-galactosidase assays were performed as previously described. At least three independent assays were performed three times independently.

Antibodies, Western blot analysis, immunocytochemistry, and immunohistochemistry. Polyclonal antibody (Ab48) was raised in a rabbit against the synthetic oliogopeptide RPSSARRHHLGPTLKPTL (SEQ ID NO.7) (amino acids 432 to 449 of RFT-A). Thirty milligrams of human tissue protein (Clontech) were run on a 8% SDS-acrylamide gel, and then transferred onto a nitrocellulose membrane. Filters were probed with Ab48 (1:1000) and visualized with the ECL detection system (Amersham).

Immunocytochemistry was performed with the anti-His tag monoclonal antibody (Qiagen) 24 hours after transfection of mammalian expression vectors. Immunohistochemistry was performed on a human glioma biopsy freshly fixed with 4% paraformaldehyde overnight, and subsequently soaked in 30% sucrose in phosphate buffered saline as a cryoprotectant. Forty millimeter sections were blocked with 10% normal donkey serum (Sigma) and 10% normal human serum (Sigma) with 0.25% triton-X-100 (Sigma), and incubated with a primary antibody, either Ab48 (1:1000) and antiglial acidic fibrillary acidic protein (GFAP) antibody (Advanced. Immunochemicals) (1:250). The sections were washed, and a secondary antibody (donkey antirabbit IgG FITC (Jackson Immunochemicals) for Ab48 and donkey antiguinea pig IgG Cy5 (Jackson Immunochemicals) for GFAP) was applied. The sections were counter-stained with 4',6-diamidino-2-phenylindole (DAPI). The specificity of Ab48 was shown by staining with prebleed serum and adsorbed immune serum. No signal was observed at a dilution of 1:1000.

In vitro translations and gel mobility shift assays. For in vitro translations, the mammalian expression vectors were incubated with ³⁵S-labeled methionine in a rabbit reticulocyte lysate as described in the manufacturer's protocol (Promega). Products were run on an 8% SDS-acrylamide gel and dried. Quantification of each product was performed using a phosphoimager (Molecular Dynamics) and adjusted based on the amount of methionine contained in each product. The same molar amount of each product was incubated with radiolabeled probes (20,000 c.p.m.) that contained the repeated "ccgaaccgcgcgaac" (SEQ ID NO.8) sequence three times, in a buffer (10 mM Hepes pH 7.5, 50 mM KCL, 1 mM DTT, 0.1% NP-40, and 3.75% glycerol). A "agcttcgatcgcgataaggatttatccttatccccatcctcga" (SEQ ID NO.9) sequence which originated mainly from FGF-2 promoter (Shibata, F., et al., 1991, *Growth Factors* 4:277–287 (−574 to −597) was used as a nonspecific competitor.

Ribonuclease protection assay (RPA).

The partial cDNA obtained by the yeast one hybrid system was subcloned into the pBluescript (Stratagene). In vitro transcription of the antisense probes and RPA were performed as described in the manufacturer's protocol (Ambion). Briefly, 100 ng of human testes polyA (Clontech) and 50 mg of total RNA of U87MG cells and 293 cells were hybridized with gel-purified probes (50,000 c.p.m.). The protected bands were loaded on a 5% native gel as double strand RNAs. A radiolabeled DNA marker of a 123 bp ladder (GIBCO BRL) was included on the gel. Images were measured by phosphoimager and RFT A/A'/B ratios were calculated using an adjustment to account for the number of ³²P-UTP contained in the protected bands.

Adeno-associated virus (AAV), reverse transcriptase polymerase chain reaction (RT-PCR), and TdT-mediated dUTP-X nick end labeling (TUNEL).

Each form of RFT was subcloned into pBKlAAV (Ishii, S., et al., 1985, *Science*, 230:1378–1381) an AAV multiple cloning vector based on the cytomegalovirus immediate early enhancer and promoter (Snyder, R. O. et al., 1997, *Human Gene Therapy* 8:1891–1900). rAAV vectors were produced by a modified transient plasmid transfection protocol followed by two rounds of cesium chloride equilibrium density gradient centrifugation and heat treatment at 56° C. for 60 minutes to destroy residual adenovirus (Zhou, S. Z., et al., 1994, *J Exp. Med.* 179:1867–1875). Titer was determined by DNA dot blot and antibody staining against the His-tag region of the inserted cDNAs. AAV carrying green fluorescent protein (GFP) (Clontech) was used as a control. Forty hours after infection (multiplicity of infection (M.O.I) of 25 for each AAV), total RNA was extracted using RNAzol B (TEL-TEST). For RT-PCR, 100 ng of total RNA was reverse transcribed by Avian Myeloblastosis Virus (AMV) reverse transcriptase (Promega) and PCR reactions were performed using Taq polymerase (Promega). The primer sets for FGF-2 and G3PDH were previously described (Care, A., et al., 1996, *Mol. Cell. Biol.*, 16:4842–4851). Linear ranges were determined by sampling the PCR products. TUNEL stainings (Boehringer Mannheim) were performed for each experiment as described in the manufacturer's protocol.

Example 2

Cloning and Transcription of RFT

To determine how human FGF-2 gene is regulated at the transcriptional level, the promoter activity of human FGF-2 was investigated in tumor cell lines. Interestingly, the human FGF-2 gene has a TATA-less promoter and its transcript is initiated at only one site (Shibata, F., et al., 1991, *Growth Factors* 4:277–287). A "gccgaac" sequence is tandemly repeated at the both sides of the transcription initiation start site of the human FGF-2 gene (FIG. 5A). Using this DNA sequence as a probe, a yeast one hybrid screen was conducted. 7×10⁶ cDNAs from human testes polyA RNA library which were intentionally generated to have short inserts. Two partial cDNAs were retrieved, one was 447 base pairs in length and one that was 40 base pairs in length. These cDNAs encoded a Cysteine (Cys) rich region that is a putative zinc finger domain (FIG. 5B). Northern blot analysis of RNA extracted from several human tissues showed that this gene was expressed ubiquitously. Two transcripts were detected: a first transcript of 3.0 kb was expressed in all tissues analyzed and a second transcript of 2.6 kb was also noted in most, but not all, of the tissues analyzed. Tissues included spleen, thymus, prostate, testis, ovary, small intestine, colon, PBLs, heart, brain, placenta, lung, liver, skeletal muscle, kidney, and pancreas. None of the three clones had a polyA tail, although the cDNA library was made using an oligo dT priming method.

The difference in size of the two transcripts could be attributed to an alternative splice site located in the 3'-untranslated region. For these assays, the RACE method (3'-rapid amplification of cDNA end) was used on human testes polyA RNA with the ORF-specific primer. All clones were digested with a restriction enzyme XbaI at the internal XbaI site in the 3'-untranslated region. The assay showed that two types of 3'-untranslated region resulted in the 3.0 kb and 2.6 kb transcripts seen in the Northern blot. This difference in the 3'untranslated region might affect the stability of mRNA.

Human testis expressed the gene abundantly, thus a human testis cDNA library (Clontech, co. Ltd.) was screened to obtain full length cDNAs, using the partial cDNA as a probe. Twelve clones were picked: one out of 12 clones was the A' form in which a lysine at position 407 is deleted. In addition, in one out of 12 clones, 58 amino acids were deleted in the putative binding domain discovered in the yeast one hybrid screen (FIG. 5B and FIG. 5C).

The gene encoding the protein discovered through the one yeast one hybrid screen was named RFT-A, and the splice variants were named RFT-A' and PFT-B. The open reading frame (ORF) is 1893 bp in RFT-A, 1890 bp in RFT-A', and 1725 nt in RFT-B Based on the genomic DNA sequence, it is likely that RFT-A' is formed by a differential splicing mechanism and RFT-B is formed by an alternative splicing mechanism of this exon. The ORFs of RFT-A, RFT-A', and RFT-B encode respectively, 630 amino acids (aa), 629 aa, and 574 aa, respectively.

Example 3

Translation and Function of RFT

In vitro translated products of RFT-A, RFT-A', and RFT-B RNAs migrated at the molecular weight of approximately 90 Kda, 90 Kda, and 75 Kda, respectively, on a denaturing gel. A Western blot analysis of human testis, brain, and kidney tissue, using a rabbit antibody generated against a synthetic oligopeptide common in the three forms (RFT Ab48), also showed that the molecular weight of RFT-A and RFT-A' forms is about 90 kda. However RFT-B form was not detected. The absence of RFT-B on the Western blot may be due to the lower level of expression in normal tissues, or may be due to a high turnover rate. Prebleed rabbit serum and preadsorbed immune serum were used as controls.

To determine the cellular localization of RFT, immunohistochemistry was performed on sections of specimen of a freshly fixed human glioma. The cells of this glioma stained positively for Glial Fibrillary Acidic Protein (GFAP) in the cytoplasm, indicating that the specimen was a mixed glioma. RFT antibody (Ab48) stained positively in the nucleus of these glioma cells, whereas the prebleed rabbit serum and adsorbed immune serum did not give a detectable signal. Taken together, these results indicate that RFT is present ubiquitously in human tissues and localizes in the nucleus of glioma tissue.

A structural analysis, shown in FIG. 5C, revealed that the RFT-A and RFT-A' forms contained two Cys-rich regions. The N-terminal Cys-rich region showed 50% similarity to the mixed-lineage leukemia (MLL) (Zeleznik-Le, N. J., et al., 1994, *Proc. Natl. Acad. Sci. USA* 91:10610–10614) and acute lymphioblastic leukemia (ALL-1) (Gu, Y., et al., 1992, *Cell* 71:701–708) genes. The C-terminal Cys-rich region, which was previously discovered in the yeast one hybrid screen, and is a putative zinc finger domain, showed 50% similarity to the ALL-1 gene, MLL genes, and to DNA methyltransferase (Suzuki, M., 1989, *J. Mol. Biol.* 203:971–983). The function of these similar regions in the MLL and ALL-1 genes is not known.

The relative electric charges of the two Cys-rich regions are different, with the region in the N-terminal Cys-rich region being negatively charged, and region in the C-terminal Cys-rich region being positively charged. The charges indicated that the C-terminal Cys-rich region is a DNA binding domain as DNA is negatively charged.

Nine serine/threonine-proline-X-X (S/TPXX) motifs Zeleznik-Le, N. J., et al., 1994, *Proc. Natl. Acad. Sci. USA* 91:10610–10614) were present in the all variants of RFT. S/TPXX motifs are reportedly found more frequently in gene regulatory proteins and are located on either side of DNA recognizing units (Suzuki, M., 1989, *J. Mol. Biol.* 207:61–84). In addition, two putative nuclear localizing signals were present near the splice region.

His-tagged expression vectors each of RFT were constructed to determine the localization of each form of RFT in cells. These expression vectors were transfected into the human glioma cell line, U87MG (ATCC, Rockville, Md.), and the human kidney tumor cell line, 293 (Graham, F. L., et al., 1977, *J. Gen. Virol.* 36:59–72). After staining by anti-His tag antibody, a confocal microscopic analysis revealed clear nuclear localization of all forms of RFT in each cell line studied. Thus, structural examination, immunohistocliemistry, and immunocytochemistry suggest that the RFT gene product is a transcription factor.

Example 4

FUNCTION OF RFT

To determine the affinity of each form of RFT for the "gccgaac" sequence, gel mobility shift assays were performed. The RFT-A form showed highly specific affinity for "gccgaac", while the RFT-A' and RFT-B forms showed significantly lower affinity to the same sequence. Thus, the structural examination, the localization study, and the DNA binding assay, suggest that the RFT gene product is a transcription factor.

To further investigate the function of RFT-A, RFT-A', and RFT-B, cotransfection experiments were performed. The experiments utilized the expression vectors containing each form of RFT, and the vector pGL1.2 F, which contains a 1.2 kb fragment of the FGF-2 promoter in a reporter construct, in U87MG and 293 cells. As an internal control, H-RASras bGAL, (Ishii, S., et al., *Science* 230:1378–1381) was also transfected. After 40 hours, luciferase and β-galactosidase assays were performed. In the U87MG cell lines, RFT-A repressed the 1.2 kb of FGF-2 promoter activity almost completely and, in the 293 cell line, RFT-A repressed the 1.2 kb of FGF-2 promoter activity completely. In contrast, in the 293 and U87MG cell lines RFT-A' and RFT-B did not repress the FGF-2 promoter activity. In the 293 cell line, RFT-A' and RFT-B forms activated FGF-2 promoter activity. In both cells lines, a dose-dependent effect of all forms of the RFT genes was observed. In control experiments, the epidermal growth factor receptor promoter was cotransfected with expression vectors containing the RFT forms. Epidermal growth factor promoter activity was not affected by any of the forms of the RFT genes.

To determine if the RFT gene product regulated the endogenous expression level of the FGF-2 gene, reverse transcriptase-polyinerase chain reaction (RT-PCR) analyses, in the linear range, were performed on the cell lines after the infection with an adeno-associated virus (AAV) expression vectors carrying each form of the RFT gene. The results were consistent with the luciferase assay in U87MG cells, and demonstrated that RFT-A suppressed FGF-2 expression, while neither RFT-A' and RFT-B fail to bind expression. These results were only qualitative, or semiquantitative. Quantitation of the level of repression and /or activation was not achieved as PCR, even in the linear range, is only semiquantitative, and the turnover rate of endogenous mRNA of FGF-2 is unknown. These results, taken together with the results showing the nuclear localization of RFT, leads to the conclusion that RFT-A can bind to the basal core promoter of the FGF-2 promoter and repress its activity, while RFT-A' and RFT-B do not repress FGF-2 transcription. This difference in function is attributable to differential and/or alternative splicing, but not to a disruption of the nuclear localization signal.

Example 5

BIOLOGICAL ACTIVITY

The PCM-1 gene from a human retinal cDNA library has been computationally cloned. This gene has homology with RFT and may be an alternatively spliced isoform of the RFT-A. PCM-1 was not cloned from the human testis library, and thus, this gene or alternatively spliced isoform is a distinct tissue-specific product. Both genes contain a methylated CpG binding domain (FIG. 5C) that can repress transcription of a methylated promoter in vitro. Therefore, the homologous methylated CpG binding region of RFT-A was truncated and cotransfected with the FGF-2 promoter into both the 293 and the U87MG cell lines. It was observed that the truncated RFT-A repressed FGF-2 promoter activity to the same level as wild type RFT-A. AAV carrying truncated RFT-A was produced and used to infect glioma cells, which induced apoptosis, as did wt RFT-A. The functions of PCM-1 and RFT are thus independent.

Figure 6A:
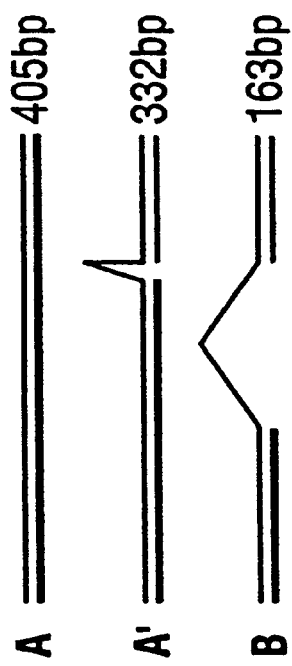

A difference in the magnitude of responsiveness to RFT-A' and RFT-B can be detected in the U87MG and 293 cell lines. In the 293 cell line, activation of FGF-2 promoter is observed. This difference may be due to the difference of the endogenous expression level of each form of the RFT gene in the two cell lines. To check the ratio of endogenous level of each form of RFT in the different cell lines, a ribonuclease protection assay (RPA) was performed using an antisense riboprobe directed to the binding region of RFT-A (FIG. 6A). In human testis, the RFT-A form is the dominant form, and the RFT A/A'/B ratio is 20/1/1. In the 293 cell line, the RFT A/A'/B ratio is 1/2/4, while in the U87MG glioma cell line, the RFT A/A'/B ratio is 1/9/44. Without meaning to be bound by theory, it is possible that RFT-A' and RFT-B forms may have dominant negative activity as to RFT-A in the 293 cells.

In order to show the biological activity, U87MG cells were infected with AAV carrying RFT-A (AAV-A). An anti-neutralizing antibody against FGF-2 has been reported to induce apoptosis into glioma cell lines (Murai, N., et al., 1996, *J. Neurosurg.* 85:1072–1077). It is, therefore, possible that expression of AAV carrying RFT-A (AAV-A) in the U87MG cells would induce a repression of FGF-2 gene expression, and would result in apoptosis. To test this hypothesis, glioma cells were infected with AAV carrying each form of the RFT gene (AAV-A, AAV-A', and AAV-B). AAV carrying the green fluorescence protein (GFP) gene (Clontech)(AAV-GFP) was used as a control. U87MG cells were also infected with AAV-A, which carries RFT-A. Only the RFT-A form induced apoptosis in the U87MG cells 96 hours after infection of AAV-A. Two additional glioma cell lines (U251MG and U373MG) were also examined and similar results were obtained. AAV carrying a truncated RFT-A was also produced and introduced into glioma cells. This truncated form also induced apoptosis in a manner similar to the wild type RFT-A.

As further evidence for specificity, RFT-A was introduced into A431 cells, as a negative control. These cells do not depend on FGF-2, and do not express FGF-2 or its receptors (Murai, N., et al., 1996, *J. Neurosurg.* 85:1072–1077). This cell line survived 96 hours after infection with AAV-A with no apoptosis or cell death above the levels of the uninfected cells.

Thus, FGF-2 gene expression is regulated by RFT-A by way of an alternative splicing mechanism in the DNA binding domain. The imbalance in the ratios of these splice variants may be one of the causes of constitutive expression of FGF-2 gene, resulting in tumor progression in FGF-2-dependent tumors. Furthermore, overexpression of the transcriptional repressor, RFT-A, induces apoptosis, when FGF-2 is deregulated in tumor cells.

A number of embodiments of the present invention have been described. Nevertheless, it will be understood that various modifications may be made without departing from the spirit and scope of the invention. Accordingly, other embodiments are within the scope of the following claims.

What is claimed is:

1. An isolated polynucleotide comprising a nucleic acid sequence encoding an amino acid sequence as set forth in SEQ ID NO:2, 4 or 6.

2. A recombinant expression vector comprising the isolated polynucleotide of claim 1.

3. The recombinant expression vector of claim 2, wherein the isolated polynucleotide is operatively linked to an expression control sequence.

4. The recombinant expression vector of claim 3, wherein the expression control sequence is selected from the group consisting of a promoter, an enhancer, a transcription factor, a stan codon, a splicing signal, and a stop codon.

5. The recombinant expression vector of claim 3, wherein the expression control sequence is a constitutive promoter or an inducible promoter.

6. The recombinant expression vector of claim 3, wherein the expression control sequence is the pL promoter of bacterlophac gamma.

7. The recombinant expression vector of claim 2, wherein the recombinant expression vector comprises the T7 expression vector.

8. The recombinant expression vector of claim 2, wherein the recombinant expression vector comprises the pMSXND expression vector.

9. An isolated host cell comprising the recombinant expression vector of claim 2.

10. An isolated polynucleotide comprising a nucleic acid sequence selected from the group consisting of:
   a) the nucleic acid sequence of SEQ ID NO:1;
   b) the nucleic acid sequence of SEQ ID NO:1, wherein T is replaced with U;
   c) the nucleic acid sequence that is the complement of SEQ ID NO:1; and
   d) an isolated polynuclcotide consisting of at least 15 nucleotides of SEQ ID NO:1 or the complement of SEQ ID NO:1, wherein the polynucleotide specifically hybridizes to SEQ ID NO:1, or the complement of SEQ ID NO:1, under highly stringent conditions, wherein said highly stringent conditions are 0.1×SSC and about 68° C.

11. An isolated polynucleotide comprising a nucleic acid sequence selected from the group consisting of:

a) the nucleic acid sequence of SEQ ID NO:3;

b) the nucleic acid sequence of SEQ ID NO:3, wherein T is replaced with U;

c) the nucleic acid sequence that is the complement of SEQ ID NO:3; and d) an isolated polynucleotide consisting of at least 15 nucleotides of SEQ ID NO:3 or the complement of SEQ ID NO:3, wherein the polynucleotide specifically hybridizes to SEQ ID NO:3, or the complement of SEQ ID NO:3, under highly stringent conditions, wherein said highly stringent conditions are 0.1×SSC and about 68° C.

12. An isolated polynucleotide comprising a nucleic acid sequence selected from the group consisting of:

a) the nucleic acid sequence of SEQ ID NO:5;

b) the nucleic acid sequence of SEQ ID NO:5, wherein T is replaced with U;

c) the nucleic acid sequence that is the complement of SEQ ID NO:5; and d) an isolated polynucleotide consisting of at least 15 nucleotides of SEQ ID NO:5 or the complement of SEQ ID NO:5, wherein the polynucleotide specifically hybridizes to SEQ ID NO:5, or the complement of SEQ ID NO:5, under highly stringent conditions, wherein said highly stringent conditions are 0.1×SSC and about 68° C.

13. An isolated polynucleotide consisting of at least 15 nucleotides of SEQ ID NO:1 or the complement of SEQ ID NO:1, wherein the polynuclcotide specifically hybridizes to SEQ ID NO:1, or the complement of SEQ ID NO:1, under highly stringent conditions, wherein said highly stringent conditions are 0.1×SSC and about 68° C.

14. An isolated polynticleotide consisting of at least 15 nucleotides of SEQ ID NO:3 or the complement of SEQ ID NO:3, wherein the polynticleotide specifically hybridizes to SEQ ID NO:3, or the complement of SEQ ID NO:3, under highly stringent conditions, wherein said highly stringent conditions are 0.1×SSC and about 68° C.

15. An isolated polynucleotide consisting of at least 15 nucleotides of SEQ ID NO:5 or the complement of SEQ ID NO:5, wherein the polynucleotide specifically hybridizes to SEQ ID NO:5, or the complement of SEQ ID NO:5, under highly stringent conditions, wherein said highly stringent conditions are 0.1×SSC and about 68° C.

* * * * *

SEQUENCE LISTING

<160> NUMBER OF SEQ ID NOS: 9

<210> SEQ ID NO 1
<211> LENGTH: 2257
<212> TYPE: DNA
<213> ORGANISM: Homo sapiens
<220> FEATURE:
<221> NAME/KEY: CDS
<222> LOCATION: (178)...(2067)

<400> SEQUENCE: 1

```
gaacagccgc ggaggcgaca gctaccgctt cagaggaggc ggccgcggag gaggaggaag        60
gggaggaggg cgaggcggga ggtgcaggag ggaccctcgc catgggtcca cgggcctaga       120
gtggcggaag ataccggcct ggtgccaaac tggctactgc tgcttcctgt ggcctcc atg      180
                                                                   Met
                                                                    1 gct gag gac tgg ctg gac tgc ccg gcc ctg ggc cct ggc tgg aag cgc        228
Ala Glu Asp Trp Leu Asp Cys Pro Ala Leu Gly Pro Gly Trp Lys Arg
        5                  10                  15
```

```
cgc gaa gtc ttt cgc aag tca ggg gcc acc tgt gga cgc tca gac acc      276
Arg Glu Val Phe Arg Lys Ser Gly Ala Thr Cys Gly Arg Ser Asp Thr
         20                  25                  30 tat tac cag agc ccc aca gga gac agg atc cga agc aaa gtt gag ctg      324
Tyr Tyr Gln Ser Pro Thr Gly Asp Arg Ile Arg Ser Lys Val Glu Leu
 35                  40                  45 act cga tac ctg ggc cct gcg tgt gat ctc acc ctc ttt gac ttc aaa      372
Thr Arg Tyr Leu Gly Pro Ala Cys Asp Leu Thr Leu Phe Asp Phe Lys
 50                  55                  60                  65 caa ggc atc ttg tgc tat cca gcc ccc aag gcc cat ccc gtg gcg gtt      420
Gln Gly Ile Leu Cys Tyr Pro Ala Pro Lys Ala His Pro Val Ala Val
                 70                  75                  80 gcc agc aag aag cga aag aag cct tca agg cca gcc aag act cgg aaa      468
Ala Ser Lys Lys Arg Lys Lys Pro Ser Arg Pro Ala Lys Thr Arg Lys
             85                  90                  95 cgt cag gtt gga ccc cag agt ggt gag gtc agg aag gag gcc ccg agg      516
Arg Gln Val Gly Pro Gln Ser Gly Glu Val Arg Lys Glu Ala Pro Arg
        100                 105                 110 gat gag acc aag gct gac act gac aca gcc cca gct tca ttc cct gct      564
Asp Glu Thr Lys Ala Asp Thr Asp Thr Ala Pro Ala Ser Phe Pro Ala
    115                 120                 125 cct ggg tgc tgt gag aac tgt gga atc agc ttc tca ggg gat ggc acc      612
Pro Gly Cys Cys Glu Asn Cys Gly Ile Ser Phe Ser Gly Asp Gly Thr
130                 135                 140                 145 caa agg cag cgg ctc aaa acg ttg tgc aaa gac tgt cga gca cag aga      660
Gln Arg Gln Arg Leu Lys Thr Leu Cys Lys Asp Cys Arg Ala Gln Arg
                150                 155                 160 att gcc ttc aac cgg gaa cag aga atg ttt aag cgt gtg ggc tgt ggg      708
Ile Ala Phe Asn Arg Glu Gln Arg Met Phe Lys Arg Val Gly Cys Gly
            165                 170                 175 gag tgt gca gcc tgc cag gta aca gaa gac tgt ggg gcc tgc tcc acc      756
Glu Cys Ala Ala Cys Gln Val Thr Glu Asp Cys Gly Ala Cys Ser Thr
        180                 185                 190 tgc ctc ctg cag ctg ccc cat gat gtg gca tcg ggg ctg ttc tgc aag      804
Cys Leu Leu Gln Leu Pro His Asp Val Ala Ser Gly Leu Phe Cys Lys
    195                 200                 205 tgt gaa cgg aga cgc tgc ctc cgg att gtg gaa agg agc cga ggg tgt      852
Cys Glu Arg Arg Arg Cys Leu Arg Ile Val Glu Arg Ser Arg Gly Cys
210                 215                 220                 225 gga gta tgc cgg ggc tgt cag acc caa gag gat tgt ggc cat tgc ccc      900
Gly Val Cys Arg Gly Cys Gln Thr Gln Glu Asp Cys Gly His Cys Pro
                230                 235                 240 atc tgc ctt cgc cct ccc cgc cct ggt ctc agg cgc cag tgg aaa tgt      948
Ile Cys Leu Arg Pro Pro Arg Pro Gly Leu Arg Arg Gln Trp Lys Cys
            245                 250                 255 gtc cag cga cgt tgc cta cgg cac ctt gct cac cgt ctg cgt cgc cgt      996
Val Gln Arg Arg Cys Leu Arg His Leu Ala His Arg Leu Arg Arg Arg
        260                 265                 270 cat cag aga tgt cag cga cgc act ccc ctg gct gtg gct ccc cca act     1044
His Gln Arg Cys Gln Arg Arg Thr Pro Leu Ala Val Ala Pro Pro Thr
    275                 280                 285 ggt aaa cat gcc cgc cgc aag gga ggc tgt gac tcc aag atg gct gcc     1092
Gly Lys His Ala Arg Arg Lys Gly Gly Cys Asp Ser Lys Met Ala Ala
290                 295                 300                 305 agg cgg cgc ccc gga gcc cag cca ctg cct cca ccc cca tca cag         1140
Arg Arg Arg Pro Gly Ala Gln Pro Leu Pro Pro Pro Pro Ser Gln
                310                 315                 320 tcc cca gag ccc aca gag ccg cac ccc aga gcc ctg gcc ccc tcg cca     1188
Ser Pro Glu Pro Thr Glu Pro His Pro Arg Ala Leu Ala Pro Ser Pro
```

-continued

```
                    325                 330                 335
cct gcc gag ttc atc tat tac tgt gta gac gag gac gag cta cag ccc      1236
Pro Ala Glu Phe Ile Tyr Tyr Cys Val Asp Glu Asp Glu Leu Gln Pro
        340                 345                 350 tac acg aac cgc cgg cag aac cgc aag tgc ggg gcc tgt gca gcc tgc      1284
Tyr Thr Asn Arg Arg Gln Asn Arg Lys Cys Gly Ala Cys Ala Ala Cys
    355                 360                 365 cta cgg cgg atg gac tgt ggc cgc tgc gac ttc tgc tgc gac aag ccc      1332
Leu Arg Arg Met Asp Cys Gly Arg Cys Asp Phe Cys Cys Asp Lys Pro
370                 375                 380                 385 aaa ttc ggg ggc agc aac cag aag cgc cag aag tgt cgt tgg cgc caa      1380
Lys Phe Gly Gly Ser Asn Gln Lys Arg Gln Lys Cys Arg Trp Arg Gln
                390                 395                 400 tgc ctg cag ttt gcc atg aag cgg ctg ctg ccc agt gtc tgg tca gag      1428
Cys Leu Gln Phe Ala Met Lys Arg Leu Leu Pro Ser Val Trp Ser Glu
            405                 410                 415 tct gag gat ggg gca gga tcg ccc cca cct tac cgt cgt cga aag agg      1476
Ser Glu Asp Gly Ala Gly Ser Pro Pro Pro Tyr Arg Arg Lys Arg
        420                 425                 430 ccc agc tct gcc cga cgg cac cat ctt ggc cct acc ttg aag ccc acc      1524
Pro Ser Ser Ala Arg Arg His His Leu Gly Pro Thr Leu Lys Pro Thr
    435                 440                 445 ttg gct aca cgc aca gcc caa cca gac cat acc cag gct cca acg aag      1572
Leu Ala Thr Arg Thr Ala Gln Pro Asp His Thr Gln Ala Pro Thr Lys
450                 455                 460                 465 cag gaa gca ggt ggt ggc ttt gtg ctg ccc ccg cct ggc act gac ctt      1620
Gln Glu Ala Gly Gly Gly Phe Val Leu Pro Pro Pro Gly Thr Asp Leu
                470                 475                 480 gtg ttt tta cgg gaa ggc gca agc agt cct gtg cag gtg ccg ggc cct      1668
Val Phe Leu Arg Glu Gly Ala Ser Ser Pro Val Gln Val Pro Gly Pro
            485                 490                 495 gtt gca gct tcc aca gaa gcc ctg ttg cag gag gcc cag tgc tct ggc      1716
Val Ala Ala Ser Thr Glu Ala Leu Leu Gln Glu Ala Gln Cys Ser Gly
        500                 505                 510 ctg agt tgg gtt gtg gcc tta ccc cag gtg aag caa gag aag gcg gat      1764
Leu Ser Trp Val Val Ala Leu Pro Gln Val Lys Gln Glu Lys Ala Asp
    515                 520                 525 acc cag gac gag tgg aca cca ggc aca gct gtc ctg act tct ccc gta      1812
Thr Gln Asp Glu Trp Thr Pro Gly Thr Ala Val Leu Thr Ser Pro Val
530                 535                 540                 545 ttg gtg cct ggc tgc cct agc aag gca gta gac cca ggc ctg cct tct      1860
Leu Val Pro Gly Cys Pro Ser Lys Ala Val Asp Pro Gly Leu Pro Ser
                550                 555                 560 gtg aag caa gag cca cct gac cca gag gag gac aag gag gag aac aag      1908
Val Lys Gln Glu Pro Pro Asp Pro Glu Glu Asp Lys Glu Glu Asn Lys
            565                 570                 575 gat gat tct gcc tcc aaa ttg gcc cca gag gaa gag gca gga ggg gct      1956
Asp Asp Ser Ala Ser Lys Leu Ala Pro Glu Glu Glu Ala Gly Gly Ala
        580                 585                 590 ggc aca ccc gtg atc acg gag att ttc agc ctg ggt gga acc cgc ttc      2004
Gly Thr Pro Val Ile Thr Glu Ile Phe Ser Leu Gly Gly Thr Arg Phe
    595                 600                 605 cga gat aca gca gtc tgg ttg cca agg tcc aaa gac ctt aaa aaa cct      2052
Arg Asp Thr Ala Val Trp Leu Pro Arg Ser Lys Asp Leu Lys Lys Pro
610                 615                 620                 625 gga gct aga aag cag tagactggag gcttctacag actgtaggat tcaaggtgat      2107
Gly Ala Arg Lys Gln
                630 atttgcagac tggctttatg agagacaaca ctgatctact aggggctgga ccctacattg    2167
```

```
gttgccaggg cttgtgtgtg aatcacccct aggaggaaaa acctactatc aaacctgaag    2227
agcaggccta agagtacttt gagcttctag                                     2257
```

<210> SEQ ID NO 2
<211> LENGTH: 630
<212> TYPE: PRT
<213> ORGANISM: Homo sapiens

<400> SEQUENCE: 2

```
Met Ala Glu Asp Trp Leu Asp Cys Pro Ala Leu Gly Pro Gly Trp Lys
 1               5                  10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg His Leu Ala His Arg Leu Arg Arg
            260                 265                 270

Arg His Gln Arg Cys Gln Arg Thr Pro Leu Ala Val Ala Pro Pro
        275                 280                 285

Thr Gly Lys His Ala Arg Arg Leu Gly Gly Cys Asp Ser Lys Met Ala
    290                 295                 300

Ala Arg Arg Arg Pro Gly Ala Gln Pro Leu Pro Pro Pro Pro Ser
305                 310                 315                 320

Gln Ser Pro Glu Pro Thr Glu Pro His Pro Arg Ala Leu Ala Pro Ser
                325                 330                 335

Pro Pro Ala Glu Phe Ile Tyr Tyr Cys Val Asp Glu Asp Glu Leu Gln
            340                 345                 350
```

```
Pro Tyr Thr Asn Arg Arg Gln Asn Arg Lys Cys Gly Ala Cys Ala Ala
        355                 360                 365

Cys Leu Arg Arg Met Asp Cys Gly Arg Cys Asp Phe Cys Cys Asp Lys
        370                 375                 380

Pro Lys Phe Gly Gly Ser Asn Gln Lys Arg Gln Lys Cys Arg Trp Arg
385                 390                 395                 400

Gln Cys Leu Gln Phe Ala Met Lys Arg Leu Leu Pro Ser Val Trp Ser
                405                 410                 415

Glu Ser Glu Asp Gly Ala Gly Ser Pro Pro Tyr Arg Arg Lys
            420                 425                 430

Arg Pro Ser Ser Ala Arg Arg His His Leu Gly Pro Thr Leu Lys Pro
        435                 440                 445

Thr Leu Ala Thr Arg Thr Ala Gln Pro Asp His Thr Gln Ala Pro Thr
    450                 455                 460

Lys Gln Glu Ala Gly Gly Gly Phe Val Leu Pro Pro Gly Thr Asp
465                 470                 475                 480

Leu Val Phe Leu Arg Glu Gly Ala Ser Ser Pro Val Gln Val Pro Gly
                485                 490                 495

Pro Val Ala Ala Ser Thr Glu Ala Leu Leu Gln Glu Ala Gln Cys Ser
                500                 505                 510

Gly Leu Ser Trp Val Val Ala Leu Pro Gln Val Lys Gln Glu Lys Ala
        515                 520                 525

Asp Thr Gln Asp Glu Trp Thr Pro Gly Thr Ala Val Leu Thr Ser Pro
    530                 535                 540

Val Leu Val Pro Gly Cys Pro Ser Lys Ala Val Asp Pro Gly Leu Pro
545                 550                 555                 560

Ser Val Lys Gln Glu Pro Pro Asp Pro Glu Asp Lys Glu Glu Asn
                565                 570                 575

Lys Asp Asp Ser Ala Ser Lys Leu Ala Pro Glu Glu Ala Gly Gly
            580                 585                 590

Ala Gly Thr Pro Val Ile Thr Glu Ile Phe Ser Leu Gly Gly Thr Arg
        595                 600                 605

Phe Arg Asp Thr Ala Val Trp Leu Pro Arg Ser Lys Asp Leu Lys Lys
    610                 615                 620

Pro Gly Ala Arg Lys Gln
625                 630

<210> SEQ ID NO 3
<211> LENGTH: 2254
<212> TYPE: DNA
<213> ORGANISM: Homo sapiens
<220> FEATURE:
<221> NAME/KEY: CDS
<222> LOCATION: (178)...(2065)

<400> SEQUENCE: 3
gaacagccgc ggaggcgaca gctaccgctt cagaggaggc ggccgcggag gaggaggaag     60
gggaggaggg cgaggcggga ggtgcaggag ggaccctcgc catgggtcca cgggcctaga    120
gtggcggaag ataccggcct ggtgccaaac tggctactgc tgcttcctgt ggcctcc atg    180
                                                             Met
                                                               1 gct gag gac tgg ctg gac tgc ccg gcc ctg ggc cct ggc tgg aag cgc      228
Ala Glu Asp Trp Leu Asp Cys Pro Ala Leu Gly Pro Gly Trp Lys Arg
            5                   10                  15 cgc gaa gtc ttt cgc aag tca ggg gcc acc tgt gga cgc tca gac acc      276
Arg Glu Val Phe Arg Lys Ser Gly Ala Thr Cys Gly Arg Ser Asp Thr
```

|  |  |  |  |  |  |  |  |  |  |  |  |  |  |  |  |
|---|---|---|---|---|---|---|---|---|---|---|---|---|---|---|---|

```
                 20                  25                  30
tat tac cag agc ccc aca gga gac agg atc cga agc aaa gtt gag ctg        324
Tyr Tyr Gln Ser Pro Thr Gly Asp Arg Ile Arg Ser Lys Val Glu Leu
         35                  40                  45 act cga tac ctg ggc cct gcg tgt gat ctc acc ctc ttt gac ttc aaa        372
Thr Arg Tyr Leu Gly Pro Ala Cys Asp Leu Thr Leu Phe Asp Phe Lys
 50                  55                  60                  65 caa ggc atc ttg tgc tat cca gcc ccc aag gcc cat ccc gtg gcg gtt        420
Gln Gly Ile Leu Cys Tyr Pro Ala Pro Lys Ala His Pro Val Ala Val
                     70                  75                  80 gcc agc aag aag cga aag aag cct tca agg cca gcc aag act cgg aaa        468
Ala Ser Lys Lys Arg Lys Lys Pro Ser Arg Pro Ala Lys Thr Arg Lys
             85                  90                  95 cgt cag gtt gga ccc cag agt ggt gag gtc agg aag gag gcc ccg agg        516
Arg Gln Val Gly Pro Gln Ser Gly Glu Val Arg Lys Glu Ala Pro Arg
        100                 105                 110 gat gag acc aag gct gac act gac aca gcc cca gct tca ttc cct gct        564
Asp Glu Thr Lys Ala Asp Thr Asp Thr Ala Pro Ala Ser Phe Pro Ala
    115                 120                 125 cct ggg tgc tgt gag aac tgt gga atc agc ttc tca ggg gat ggc acc        612
Pro Gly Cys Cys Glu Asn Cys Gly Ile Ser Phe Ser Gly Asp Gly Thr
130                 135                 140                 145 caa agg cag cgg ctc aaa acg ttg tgc aaa gac tgt cga gca cag aga        660
Gln Arg Gln Arg Leu Lys Thr Leu Cys Lys Asp Cys Arg Ala Gln Arg
                150                 155                 160 att gcc ttc aac cgg gaa cag aga atg ttt aag cgt gtg ggc tgt ggg        708
Ile Ala Phe Asn Arg Glu Gln Arg Met Phe Lys Arg Val Gly Cys Gly
            165                 170                 175 gag tgt gca gcc tgc cag gta aca gaa gac tgt ggg gcc tgc tcc acc        756
Glu Cys Ala Ala Cys Gln Val Thr Glu Asp Cys Gly Ala Cys Ser Thr
        180                 185                 190 tgc ctc ctg cag ctg ccc cat gat gtg gca tcg ggg ctg ttc tgc aag        804
Cys Leu Leu Gln Leu Pro His Asp Val Ala Ser Gly Leu Phe Cys Lys
    195                 200                 205 tgt gaa cgg aga cgc tgc ctc cgg att gtg gaa agg agc cga ggg tgt        852
Cys Glu Arg Arg Arg Cys Leu Arg Ile Val Glu Arg Ser Arg Gly Cys
210                 215                 220                 225 gga gta tgc cgg ggc tgt cag acc caa gag gat tgt ggc cat tgc ccc        900
Gly Val Cys Arg Gly Cys Gln Thr Gln Glu Asp Cys Gly His Cys Pro
                230                 235                 240 atc tgc ctt cgc cct ccc cgc cct ggt ctc agg cgc cag tgg aaa tgt        948
Ile Cys Leu Arg Pro Pro Arg Pro Gly Leu Arg Arg Gln Trp Lys Cys
            245                 250                 255 gtc cag cga cgt tgc cta cgg cac ctt gct cac cgt ctg cgt cgc cgt        996
Val Gln Arg Arg Cys Leu Arg His Leu Ala His Arg Leu Arg Arg Arg
        260                 265                 270 cat cag aga tgt cag cga cgc act ccc ctg gct gtg gct ccc cca act       1044
His Gln Arg Cys Gln Arg Arg Thr Pro Leu Ala Val Ala Pro Pro Thr
    275                 280                 285 ggt aaa cat gcc cgc cgc aag gga ggc tgt gac tcc aag atg gct gcc       1092
Gly Lys His Ala Arg Arg Lys Gly Gly Cys Asp Ser Lys Met Ala Ala
290                 295                 300                 305 agg cgg cgc ccc gga gcc cag cca ctg cct cca cca ccc cca tca cag       1140
Arg Arg Arg Pro Gly Ala Gln Pro Leu Pro Pro Pro Pro Pro Ser Gln
                310                 315                 320 tcc cca gag ccc aca gag ccg cac ccc aga gcc ctg gcc ccc tcg cca       1188
Ser Pro Glu Pro Thr Glu Pro His Pro Arg Ala Leu Ala Pro Ser Pro
            325                 330                 335 cct gcc gag ttc atc tat tac tgt gta gac gag gac gag cta cag ccc       1236
```

```
                                                        -continued

Pro Ala Glu Phe Ile Tyr Tyr Cys Val Asp Glu Asp Glu Leu Gln Pro
            340                 345                 350 tac acg aac cgc cgg cag aac cgc aag tgc ggg gcc tgt gca gcc tgc    1284
Tyr Thr Asn Arg Arg Gln Asn Arg Lys Cys Gly Ala Cys Ala Ala Cys
        355                 360                 365 cta cgg cgg atg gac tgt ggc cgc tgc gac ttc tgc tgc gac aag ccc    1332
Leu Arg Arg Met Asp Cys Gly Arg Cys Asp Phe Cys Cys Asp Lys Pro
370                 375                 380                 385 aaa ttc ggg ggc agc aac cag aag cgc cag aag tgt cgt tgg cgc caa    1380
Lys Phe Gly Gly Ser Asn Gln Lys Arg Gln Lys Cys Arg Trp Arg Gln
                390                 395                 400 tgc ctg cag ttt gcc atg cgg ctg ctg ccc agt gtc tgg tca gag tct    1428
Cys Leu Gln Phe Ala Met Arg Leu Leu Pro Ser Val Trp Ser Glu Ser
            405                 410                 415 gag gat ggg gca gga tcg ccc cca cct tac cgt cgt cga aag agg ccc    1476
Glu Asp Gly Ala Gly Ser Pro Pro Pro Tyr Arg Arg Arg Lys Arg Pro
        420                 425                 430 agc tct gcc cga cgg cac cat ctt ggc cct acc ttg aag ccc acc ttg    1524
Ser Ser Ala Arg Arg His His Leu Gly Pro Thr Leu Lys Pro Thr Leu
    435                 440                 445 gct aca cgc aca gcc caa cca gac cat acc cag gct cca acg aag cag    1572
Ala Thr Arg Thr Ala Gln Pro Asp His Thr Gln Ala Pro Thr Lys Gln
450                 455                 460                 465 gaa gca ggt ggt ggc ttt gtg ctg ccc ccg cct ggc act gac ctt gtg    1620
Glu Ala Gly Gly Gly Phe Val Leu Pro Pro Pro Gly Thr Asp Leu Val
                470                 475                 480 ttt tta cgg gaa ggc gca agc agt cct gtg cag gtg ccg ggc cct gtt    1668
Phe Leu Arg Glu Gly Ala Ser Ser Pro Val Gln Val Pro Gly Pro Val
            485                 490                 495 gca gct tcc aca gaa gcc ctg ttg cag gag gcc cag tgc tct ggc ctg    1716
Ala Ala Ser Thr Glu Ala Leu Leu Gln Glu Ala Gln Cys Ser Gly Leu
        500                 505                 510 agt tgg gtt gtg gcc tta ccc cag gtg aag caa gag aag gcg gat acc    1764
Ser Trp Val Val Ala Leu Pro Gln Val Lys Gln Glu Lys Ala Asp Thr
    515                 520                 525 cag gac gag tgg aca cca ggc aca gct gtc ctg act tct ccc gta ttg    1812
Gln Asp Glu Trp Thr Pro Gly Thr Ala Val Leu Thr Ser Pro Val Leu
530                 535                 540                 545 gtg cct ggc tgc cct agc aag gca gta gac cca ggc ctg cct tct gtg    1860
Val Pro Gly Cys Pro Ser Lys Ala Val Asp Pro Gly Leu Pro Ser Val
                550                 555                 560 aag caa gag cca cct gac cca gag gag gac aag gag gag aac aag gat    1908
Lys Gln Glu Pro Pro Asp Pro Glu Glu Asp Lys Glu Glu Asn Lys Asp
            565                 570                 575 gat tct gcc tcc aaa ttg gcc cca gag gaa gag gca gga ggg gct ggc    1956
Asp Ser Ala Ser Lys Leu Ala Pro Glu Glu Glu Ala Gly Gly Ala Gly
        580                 585                 590 aca ccc gtg atc acg gag att ttc agc ctg ggt gga acc cgc ttc cga    2004
Thr Pro Val Ile Thr Glu Ile Phe Ser Leu Gly Gly Thr Arg Phe Arg
    595                 600                 605 gat aca gca gtc tgg ttg cca agg tcc aaa gac ctt aaa aaa cct gga    2052
Asp Thr Ala Val Trp Leu Pro Arg Ser Lys Asp Leu Lys Lys Pro Gly
610                 615                 620                 625 gct aga aag cag tag actggaggct tctacagact gtaggattca aggtgata    2105
Ala Arg Lys Gln tttgcagact ggctttatga gagacaacac tgatctacta ggggctggac cctacattgg   2165
ttgccagggc ttgtgtgtga atcaccccta ggaggaaaaa cctactatca aacctgaaga   2225
gcaggcctaa gagtactttg agcttctag                                     2254
```

```
<210> SEQ ID NO 4
<211> LENGTH: 629
<212> TYPE: PRT
<213> ORGANISM: Homo sapiens

<400> SEQUENCE: 4

Met Ala Glu Asp Trp Leu Asp Cys Pro Ala Leu Gly Pro Gly Trp Lys
 1               5                  10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg His Leu Ala His Arg Leu Arg Arg
            260                 265                 270

Arg His Gln Arg Cys Gln Arg Thr Pro Leu Ala Val Ala Pro Pro
        275                 280                 285

Thr Gly Lys His Ala Arg Arg Lys Gly Gly Cys Asp Ser Lys Met Ala
    290                 295                 300

Ala Arg Arg Arg Pro Gly Ala Gln Pro Leu Pro Pro Pro Pro Ser
305                 310                 315                 320

Gln Ser Pro Glu Pro Thr Glu Pro His Pro Arg Ala Leu Ala Pro Ser
                325                 330                 335

Pro Pro Ala Glu Phe Ile Tyr Tyr Cys Val Asp Glu Asp Glu Leu Gln
            340                 345                 350

Pro Tyr Thr Asn Arg Arg Gln Asn Arg Lys Cys Gly Ala Cys Ala Ala
        355                 360                 365

Cys Leu Arg Arg Met Asp Cys Gly Arg Cys Asp Phe Cys Cys Asp Lys
```

```
                   370             375             380
Pro Lys Phe Gly Gly Ser Asn Gln Lys Arg Gln Lys Cys Arg Trp Arg
385                 390                 395                 400

Gln Cys Leu Gln Phe Ala Met Arg Leu Leu Pro Ser Val Trp Ser Glu
                405                 410                 415

Ser Glu Asp Gly Ala Gly Ser Pro Pro Tyr Arg Arg Lys Arg
            420                 425                 430

Pro Ser Ser Ala Arg Arg His His Leu Gly Pro Thr Leu Lys Pro Thr
        435                 440                 445

Leu Ala Thr Arg Thr Ala Gln Pro Asp His Thr Gln Ala Pro Thr Lys
    450                 455                 460

Gln Glu Ala Gly Gly Phe Val Leu Pro Pro Gly Thr Asp Leu
465                 470                 475                 480

Val Phe Leu Arg Glu Gly Ala Ser Ser Pro Val Gln Val Pro Gly Pro
                485                 490                 495

Val Ala Ala Ser Thr Glu Ala Leu Leu Gln Glu Ala Gln Cys Ser Gly
            500                 505                 510

Leu Ser Trp Val Val Ala Leu Pro Gln Val Lys Gln Glu Lys Ala Asp
        515                 520                 525

Thr Gln Asp Glu Trp Thr Pro Gly Thr Ala Val Leu Thr Ser Pro Val
    530                 535                 540

Leu Val Pro Gly Cys Pro Ser Lys Ala Val Asp Pro Gly Leu Pro Ser
545                 550                 555                 560

Val Lys Gln Glu Pro Pro Asp Pro Glu Glu Asp Lys Glu Glu Asn Lys
                565                 570                 575

Asp Asp Ser Ala Ser Lys Leu Ala Pro Glu Glu Glu Ala Gly Gly Ala
            580                 585                 590

Gly Thr Pro Val Ile Thr Glu Ile Phe Ser Leu Gly Gly Thr Arg Phe
        595                 600                 605

Arg Asp Thr Ala Val Trp Leu Pro Arg Ser Lys Asp Leu Lys Lys Pro
    610                 615                 620

Gly Ala Arg Lys Gln
625

<210> SEQ ID NO 5
<211> LENGTH: 2089
<212> TYPE: DNA
<213> ORGANISM: Homo sapiens
<220> FEATURE:
<221> NAME/KEY: CDS
<222> LOCATION: (178)...(1899)

<400> SEQUENCE: 5
gaacagccgc ggaggcgaca gctaccgctt cagaggaggc ggccgcggag gaggaggaag      60
gggaggaggg cgaggcggga ggtgcaggag ggaccctcgc catgggtcca cgggcctaga    120
gtggcggaag ataccggcct ggtgccaaac tggctactgc tgcttcctgt ggcctcc atg   180
                                                            Met
                                                              1 gct gag gac tgg ctg gac tgc ccg gcc ctg ggc cct ggc tgg aag cgc      228
Ala Glu Asp Trp Leu Asp Cys Pro Ala Leu Gly Pro Gly Trp Lys Arg
          5                  10                  15 cgc gaa gtc ttt cgc aag tca ggg gcc acc tgt gga cgc tca gac acc      276
Arg Glu Val Phe Arg Lys Ser Gly Ala Thr Cys Gly Arg Ser Asp Thr
             20                  25                  30 tat tac cag agc ccc aca gga gac agg atc cga agc aaa gtt gag ctg      324
Tyr Tyr Gln Ser Pro Thr Gly Asp Arg Ile Arg Ser Lys Val Glu Leu
```

```
              35                  40                  45
act cga tac ctg ggc cct gcg tgt gat ctc acc ctc ttt gac ttc aaa        372
Thr Arg Tyr Leu Gly Pro Ala Cys Asp Leu Thr Leu Phe Asp Phe Lys
 50              55                  60                  65 caa ggc atc ttg tgc tat cca gcc ccc aag gcc cat ccc gtg gcg gtt        420
Gln Gly Ile Leu Cys Tyr Pro Ala Pro Lys Ala His Pro Val Ala Val
             70                  75                  80 gcc agc aag aag cga aag aag cct tca agg cca gcc aag act cgg aaa        468
Ala Ser Lys Lys Arg Lys Lys Pro Ser Arg Pro Ala Lys Thr Arg Lys
             85                  90                  95 cgt cag gtt gga ccc cag agt ggt gag gtc agg aag gag gcc ccg agg        516
Arg Gln Val Gly Pro Gln Ser Gly Glu Val Arg Lys Glu Ala Pro Arg
            100                 105                 110 gat gag acc aag gct gac act gac aca gcc cca gct tca ttc cct gct        564
Asp Glu Thr Lys Ala Asp Thr Asp Thr Ala Pro Ala Ser Phe Pro Ala
            115                 120                 125 cct ggg tgc tgt gag aac tgt gga atc agc ttc tca ggg gat ggc acc        612
Pro Gly Cys Cys Glu Asn Cys Gly Ile Ser Phe Ser Gly Asp Gly Thr
130             135                 140                 145 caa agg cag cgg ctc aaa acg ttg tgc aaa gac tgt cga gca cag aga        660
Gln Arg Gln Arg Leu Lys Thr Leu Cys Lys Asp Cys Arg Ala Gln Arg
            150                 155                 160 att gcc ttc aac cgg gaa cag aga atg ttt aag cgt gtg ggc tgt ggg        708
Ile Ala Phe Asn Arg Glu Gln Arg Met Phe Lys Arg Val Gly Cys Gly
            165                 170                 175 gag tgt gca gcc tgc cag gta aca gaa gac tgt ggg gcc tgc tcc acc        756
Glu Cys Ala Ala Cys Gln Val Thr Glu Asp Cys Gly Ala Cys Ser Thr
            180                 185                 190 tgc ctc ctg cag ctg ccc cat gat gtg gca tcg ggg ctg ttc tgc aag        804
Cys Leu Leu Gln Leu Pro His Asp Val Ala Ser Gly Leu Phe Cys Lys
195             200                 205 tgt gaa cgg aga cgc tgc ctc cgg att gtg gaa agg agc cga ggg tgt        852
Cys Glu Arg Arg Arg Cys Leu Arg Ile Val Glu Arg Ser Arg Gly Cys
210             215                 220                 225 gga gta tgc cgg ggc tgt cag acc caa gag gat tgt ggc cat tgc ccc        900
Gly Val Cys Arg Gly Cys Gln Thr Gln Glu Asp Cys Gly His Cys Pro
            230                 235                 240 atc tgc ctt cgc cct ccc cgc cct ggt ctc agg cgc cag tgg aaa tgt        948
Ile Cys Leu Arg Pro Pro Arg Pro Gly Leu Arg Arg Gln Trp Lys Cys
            245                 250                 255 gtc cag cga cgt tgc cta cgg cac ctt gct cac cgt ctg cgt cgc cgt        996
Val Gln Arg Arg Cys Leu Arg His Leu Ala His Arg Leu Arg Arg Arg
            260                 265                 270 cat cag aga tgt cag cga cgc act ccc ctg gct gtg gct ccc cca act       1044
His Gln Arg Cys Gln Arg Arg Thr Pro Leu Ala Val Ala Pro Pro Thr
            275                 280                 285 ggt aaa cat gcc cgc cgc aag gga ggc tgt gac tcc aag atg gct gcc       1092
Gly Lys His Ala Arg Arg Lys Gly Gly Cys Asp Ser Lys Met Ala Ala
290             295                 300                 305 agg cgg cgc ccc gga gcc cag cca ctg cct cca cca ccc cca tca cag       1140
Arg Arg Arg Pro Gly Ala Gln Pro Leu Pro Pro Pro Pro Pro Ser Gln
            310                 315                 320 tcc cca gag ccc aca gag ccg cac ccc aga gcc ctg gcc ccc tcg cca       1188
Ser Pro Glu Pro Thr Glu Pro His Pro Arg Ala Leu Ala Pro Ser Pro
            325                 330                 335 cct gcc gag ttc atc tat tac tgt gta gac gag gac gag cta aag cgg       1236
Pro Ala Glu Phe Ile Tyr Tyr Cys Val Asp Glu Asp Glu Leu Lys Arg
            340                 345                 350 ctg ctg ccc agt gtc tgg tca gag tct gag gat ggg gca gga tcg ccc       1284
```

```
Leu Leu Pro Ser Val Trp Ser Glu Ser Glu Asp Gly Ala Gly Ser Pro
            355                 360                 365 cca cct tac cgt cgt cga aag agg ccc agc tct gcc cga cgg cac cat    1332
Pro Pro Tyr Arg Arg Arg Lys Arg Pro Ser Ser Ala Arg Arg His His
370                 375                 380                 385 ctt ggc cct acc ttg aag ccc acc ttg gct aca cgc aca gcc caa cca    1380
Leu Gly Pro Thr Leu Lys Pro Thr Leu Ala Thr Arg Thr Ala Gln Pro
                390                 395                 400 gac cat acc cag gct cca acg aag cag gaa gca ggt ggt ggc ttt gtg    1428
Asp His Thr Gln Ala Pro Thr Lys Gln Glu Ala Gly Gly Gly Phe Val
            405                 410                 415 ctg ccc ccg cct ggc act gac ctt gtg ttt tta cgg gaa ggc gca agc    1476
Leu Pro Pro Pro Gly Thr Asp Leu Val Phe Leu Arg Glu Gly Ala Ser
        420                 425                 430 agt cct gtg cag gtg ccg ggc cct gtt gca gct tcc aca gaa gcc ctg    1524
Ser Pro Val Gln Val Pro Gly Pro Val Ala Ala Ser Thr Glu Ala Leu
    435                 440                 445 ttg cag gag gcc cag tgc tct ggc ctg agt tgg gtt gtg gcc tta ccc    1572
Leu Gln Glu Ala Gln Cys Ser Gly Leu Ser Trp Val Val Ala Leu Pro
450                 455                 460                 465 cag gtg aag caa gag aag gcg gat acc cag gac gag tgg aca cca ggc    1620
Gln Val Lys Gln Glu Lys Ala Asp Thr Gln Asp Glu Trp Thr Pro Gly
                470                 475                 480 aca gct gtc ctg act tct ccc gta ttg gtg cct ggc tgc cct agc aag    1668
Thr Ala Val Leu Thr Ser Pro Val Leu Val Pro Gly Cys Pro Ser Lys
            485                 490                 495 gca gta gac cca ggc ctg cct tct gtg aag caa gag cca cct gac cca    1716
Ala Val Asp Pro Gly Leu Pro Ser Val Lys Gln Glu Pro Pro Asp Pro
        500                 505                 510 gag gag gac aag gag gag aac aag gat gat tct gcc tcc aaa ttg gcc    1764
Glu Glu Asp Lys Glu Glu Asn Lys Asp Asp Ser Ala Ser Lys Leu Ala
    515                 520                 525 cca gag gaa gag gca gga ggg gct ggc aca ccc gtg atc acg gag att    1812
Pro Glu Glu Glu Ala Gly Gly Ala Gly Thr Pro Val Ile Thr Glu Ile
530                 535                 540                 545 ttc agc ctg ggt gga acc cgc ttc cga gat aca gca gtc tgg ttg cca    1860
Phe Ser Leu Gly Gly Thr Arg Phe Arg Asp Thr Ala Val Trp Leu Pro
                550                 555                 560 agg tcc aaa gac ctt aaa aaa cct gga gct aga aag cag tagactggag     1909
Arg Ser Lys Asp Leu Lys Lys Pro Gly Ala Arg Lys Gln
            565                 570 gcttctacag actgtaggat tcaaggtgat atttgcagac tggctttatg agagacaaca  1969
ctgatctact agggctgga ccctacattg gttgccaggg cttgtgtgtg aatcacccct   2029
aggaggaaaa acctactatc aaacctgaag agcaggccta agagtacttt gagcttctag  2089

<210> SEQ ID NO 6
<211> LENGTH: 574
<212> TYPE: PRT
<213> ORGANISM: Homo sapiens

<400> SEQUENCE: 6

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
                20                  25                  30

Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
```

-continued

```
            50                  55                  60
Lys Gln Gly Ile Leu Cys Tyr Pro Ala Pro Lys Ala His Pro Val Ala
65                  70                  75                  80

Val Ala Ser Lys Lys Arg Lys Pro Ser Arg Pro Ala Lys Thr Arg
                85                  90                  95

Lys Arg Gln Val Gly Pro Gln Ser Gly Glu Val Arg Lys Glu Ala Pro
                100                 105                 110

Arg Asp Glu Thr Lys Ala Asp Thr Asp Thr Ala Pro Ala Ser Phe Pro
                115                 120                 125

Ala Pro Gly Cys Cys Glu Asn Cys Gly Ile Ser Phe Ser Gly Asp Gly
130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
                180                 185                 190

Thr Cys Leu Leu Gln Leu Pro His Asp Val Ala Ser Gly Leu Phe Cys
            195                 200                 205

Lys Cys Glu Arg Arg Arg Cys Leu Arg Ile Val Glu Arg Ser Arg Gly
210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg His Leu Ala His Arg Leu Arg Arg
                260                 265                 270

Arg His Gln Arg Cys Gln Arg Arg Thr Pro Leu Ala Val Ala Pro Pro
                275                 280                 285

Thr Gly Lys His Ala Arg Arg Lys Gly Gly Cys Asp Ser Lys Met Ala
290                 295                 300

Ala Arg Arg Arg Pro Gly Ala Gln Pro Leu Pro Pro Pro Pro Pro Ser
305                 310                 315                 320

Gln Ser Pro Glu Pro Thr Glu Pro His Pro Arg Ala Leu Ala Pro Ser
                325                 330                 335

Pro Pro Ala Glu Phe Ile Tyr Tyr Cys Val Asp Glu Asp Glu Leu Lys
                340                 345                 350

Arg Leu Leu Pro Ser Val Trp Ser Glu Ser Glu Asp Gly Ala Gly Ser
                355                 360                 365

Pro Pro Pro Tyr Arg Arg Arg Lys Arg Pro Ser Ser Ala Arg Arg His
                370                 375                 380

His Leu Gly Pro Thr Leu Lys Pro Thr Leu Ala Thr Arg Thr Ala Gln
385                 390                 395                 400

Pro Asp His Thr Gln Ala Pro Thr Lys Gln Glu Ala Gly Gly Gly Phe
                405                 410                 415

Val Leu Pro Pro Pro Gly Thr Asp Leu Val Phe Leu Arg Glu Gly Ala
                420                 425                 430

Ser Ser Pro Val Gln Val Pro Gly Pro Val Ala Ala Ser Thr Glu Ala
                435                 440                 445

Leu Leu Gln Glu Ala Gln Cys Ser Gly Leu Ser Trp Val Val Ala Leu
                450                 455                 460

Pro Gln Val Lys Gln Glu Lys Ala Asp Thr Gln Asp Glu Trp Thr Pro
465                 470                 475                 480
```

```
Gly Thr Ala Val Leu Thr Ser Pro Val Leu Val Pro Gly Cys Pro Ser
            485                 490                 495

Lys Ala Val Asp Pro Gly Leu Pro Ser Val Lys Gln Glu Pro Pro Asp
            500                 505                 510

Pro Glu Glu Asp Lys Glu Glu Asn Lys Asp Asp Ser Ala Ser Lys Leu
        515                 520                 525

Ala Pro Glu Glu Glu Ala Gly Gly Ala Gly Thr Pro Val Ile Thr Glu
    530                 535                 540

Ile Phe Ser Leu Gly Gly Thr Arg Phe Arg Asp Thr Ala Val Trp Leu
545                 550                 555                 560

Pro Arg Ser Lys Asp Leu Lys Lys Pro Gly Ala Arg Lys Gln
                565                 570

<210> SEQ ID NO 7
<211> LENGTH: 18
<212> TYPE: PRT
<213> ORGANISM: Homo sapiens

<400> SEQUENCE: 7

Arg Pro Ser Ser Ala Arg Arg His His Leu Gly Pro Thr Leu Lys Pro
1               5                   10                  15

Thr Leu

<210> SEQ ID NO 8
<211> LENGTH: 15
<212> TYPE: DNA
<213> ORGANISM: Homo sapiens

<400> SEQUENCE: 8
gccgaaccgc cgaac                                                     15

<210> SEQ ID NO 9
<211> LENGTH: 43
<212> TYPE: DNA
<213> ORGANISM: Homo sapiens

<400> SEQUENCE: 9
agcttcgatc gcgataagga tttatcctta tccccatcct cga                      43
```